(12) United States Patent
Glaser et al.

(10) Patent No.: US 8,377,192 B2
(45) Date of Patent: Feb. 19, 2013

(54) STABILISERS FOR INANIMATE ORGANIC MATERIALS

(75) Inventors: Alban Glaser, Mannheim (DE); Sylke Haremza, Neckargemuend (DE); Simon Schambony, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 26 days.

(21) Appl. No.: 13/060,705

(22) PCT Filed: Aug. 14, 2009

(86) PCT No.: PCT/EP2009/060531
§ 371 (c)(1),
(2), (4) Date: May 19, 2011

(87) PCT Pub. No.: WO2010/023115
PCT Pub. Date: Mar. 4, 2010

(65) Prior Publication Data
US 2011/0214590 A1      Sep. 8, 2011

(30) Foreign Application Priority Data

Aug. 28, 2008   (EP) ..................... 08163194

(51) Int. Cl.
C09D 7/12      (2006.01)
C08K 5/3435    (2006.01)
C07D 401/12    (2006.01)
C07D 211/56    (2006.01)

(52) U.S. Cl. .................. 106/287.2; 524/102; 524/99

(58) Field of Classification Search .................. None
See application file for complete search history.

(56) References Cited

U.S. PATENT DOCUMENTS

| | | | |
|---|---|---|---|
| 4,325,863 A | 4/1982 | Hinsken et al. | |
| 4,338,244 A | 7/1982 | Hinsken et al. | |
| 4,579,906 A | 4/1986 | Zabrocki et al. | |
| 5,004,770 A | 4/1991 | Cortolano et al. | |
| 5,096,950 A | 3/1992 | Galbo et al. | |
| 5,175,312 A | 12/1992 | Dubs et al. | |
| 5,216,052 A | 6/1993 | Nesvadba et al. | |
| 5,252,643 A | 10/1993 | Nesvadba | |
| 5,393,812 A | 2/1995 | Haley et al. | |
| 5,844,029 A | 12/1998 | Prabhu et al. | |
| 5,880,191 A | 3/1999 | Prabhu et al. | |

FOREIGN PATENT DOCUMENTS

| | | |
|---|---|---|
| DE | 43 16 611 | 11/1993 |
| DE | 43 16 622 | 11/1993 |
| DE | 43 16 876 | 11/1993 |
| DE | 101 60 602 | 6/2002 |
| EP | 0 309 402 | 3/1989 |
| EP | 0 316 582 | 5/1989 |
| EP | 0 589 839 | 3/1994 |
| EP | 0 591 102 | 4/1994 |
| EP | 0 916 335 | 5/1999 |
| WO | 94 12544 | 6/1994 |
| WO | 2008 003602 | 1/2008 |

OTHER PUBLICATIONS

International Search Report issued Jan. 4, 2010 in PCT/EP09/060531 filed Aug. 14, 2009.

*Primary Examiner* — Melvin C Mayes
*Assistant Examiner* — Yun Qian
(74) *Attorney, Agent, or Firm* — Oblon, Spivak, McClelland, Maier & Neustadt, L.L.P.

(57) ABSTRACT

The present invention relates to the use of sterically hindered amines comprising one or more groups of the general formula (I)

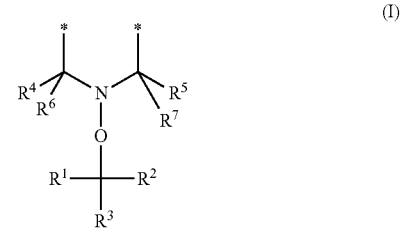

to stabilize inanimate organic material, more particularly plastics or coating materials, where $R^1$ and $R^2$ each independently, alike or different, are H, $C_1$-$C_{20}$ alkyl, $C_3$-$C_{15}$ cycloalkyl, aryl, hetaryl or a heterocycle, $R^4$, $R^5$, $R^6$, and $R^7$ each independently, alike or different, are $C_1$-$C_{20}$ alkyl, or $R^4$ and $R^6$ or $R^5$ and $R^7$ together are a tetramethylene or pentamethylene group, and $R^3$ is aryl or hetaryl. The invention further relates to methods of stabilizing inanimate organic material, especially plastics or coating materials. Additionally provided by the invention are selected sterically hindered amines comprising one or more groups of the general formula (I). Additionally provided by the invention are materials that comprise selected sterically hindered amines.

2 Claims, No Drawings

STABILISERS FOR INANIMATE ORGANIC MATERIALS

The present invention relates to the use of a sterically hindered amine comprising one or more groups Of the general formula (I)

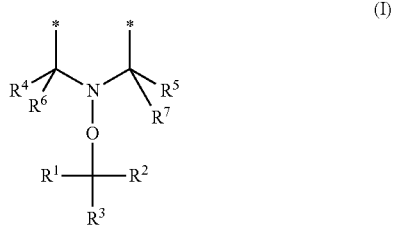

to stabilize inanimate organic material, especially plastics or coating materials, where, $R^1$ and $R^2$ each independently, alike or different are H, $C_1$-$C_{20}$ alkyl, $C_3$-$C_{15}$ cycloalkyl, aryl, hetaryl, or a heterocycle, $R^4$, $R^5$, $R^6$, and $R^7$ each independently, alike or different, $C_1$-$C_{20}$ alkyl, or $R^4$ and $R^6$ or $R^5$ and $R^7$ together are a tetramethylene or pentamethylene group, and $R^3$ is aryl or hetaryl, and where $R^1$ to $R^7$ may each be interrupted at any position by one or more heteroatoms, the number of these heteroatoms being not more than 10, preferably not more than 8, very preferably not more than 5 and in particular not more than 3, and/or may each be substituted at any position, though not more than five times, preferably not more than four times and more preferably not more than three times, by hydroxyl, amino, mono- or di-$C_1$-$C_{20}$ alkylamino, nitro, cyano, $CO_2M^1$, $CONM^1M^2$, $SO_3M^1$, $C_1$-$C_{20}$ alkyl, $C_1$-$C_{20}$ alkoxy, aryl, a heterocycle, heteroatoms or halogen, which likewise may be substituted at most two times, preferably at most one time, by the stated groups, and $M^1$, $M^2$ each independently, alike or different, are H, or $C_1$-$C_{20}$ alkyl.

The invention also relates to methods of stabilizing inanimate organic material, especially plastics or coating materials, using sterically hindered amines comprising one or more groups of the general formula (I).

Further provided by the invention are selected sterically hindered amines comprising one or more groups of the general formula (I). Additionally provided by the invention are materials which comprise selected sterically hindered amines comprising one or more groups of the general formula (I).

Inanimate organic materials are preferably stabilized by protecting these materials from adverse effects of electromagnetic radiation, especially light, heat or free radicals, especially oxygen.

Further embodiments of the present invention are apparent from the claims, description and examples. It will be appreciated that the features specified above and those still to be elucidated below, of the subject matter of the invention, can be used not only in the specific combination indicated but also in other combinations without departing the scope of the invention. Preference and particular preference are given to those embodiments of the present invention in which all of the features have the preferred, and particularly preferred definitions, respectively.

EP 0 309 402 A1 describes hindered amines based on 2,2,6,6-tetraalkylated, nitrogen-comprising heterocyclic groups, the hindered ring nitrogen atom being substituted by OR groups and it being possible for the 4 position of the ring to be substituted by a multiplicity of different groups. These hindered amines find use according to EP 0 309 402 A1 as light stabilizers in various substrates, especially thermoplastics.

U.S. Pat. No. 5,004,770 likewise describes hindered amines based on 2,2,6,6-tetraalkylated nitrogen-comprising heterocyclic groups, the hindered ring nitrogen atom being substituted by OH or OR groups and it being possible for the 4 position of the ring to be substituted by a multiplicity of different groups. These hindered amines find use according to U.S. Pat. No. 5,004,770 as stabilizers against the influence of light, heat or oxygen in various substrates which are not polyolefins.

U.S. Pat. No. 5,096,950 describes the use of sterically hindered amines based on 2,2,6,6-tetraalkylated nitrogen-comprising heterocyclic groups, the hindered ring nitrogen atom being substituted by OR groups and it being possible for the 4 position of the ring to be substituted by a multiplicity of different groups, as stabilizers against the influence of light, heat or oxygen in polyolefins.

DE 101 60 602 A1 relates to thermoplastic organic polymers, especially polyolefins, which are stabilized against the harmful effects of light, oxygen and heat and comprise a defined flame retardant comprising a sterically hindered amine of the hydrocarbyloxyamine or hydroxyhydrocarbyloxyamine class. DE 101 60 602 A1 further describes the use of these flame retardants and of the sterically hindered amines in order to light-stabilize and flame-retard thermoplastic organic polymers.

Light stabilizers based on hindered amines which are substituted on the hindered nitrogen atom by various kinds of OR groups are therefore prior art.

Often unsatisfactory are the deficient compatibility of the hindered amines with polyolefins and other plastics and also the incompatibility with acids or with materials which form acids on exposure to light and/or heat; the duration of the protective effect; the inherent color of the substances; and the thermal decomposition of the stabilizers when incorporated into polymers at an elevated temperature.

It is an object of the invention, therefore, to provide further stabilizers based on hindered amines that bring further improvement in the duration of the stabilization of inanimate organic material but that also exhibit high compatibility with the materials to be stabilized such as polyolefins and other plastics, low inherent color, and stability when incorporated into the material to be stabilized.

As is evident from the disclosure content of the present invention, these and other objects are achieved by the various embodiments of the inventive use of the above-described sterically hindered amines comprising one or more groups of the general formula (I).

In the context of the inventive use, it will be appreciated that mixtures of sterically hindered amines comprising one or more groups of the general formula (I) can also be used.

In the context of the inventive uses, the sterically hindered amines comprising one or more groups of the general formula (I) exhibit no inherent color, are highly compatible with a very wide variety of inanimate organic materials, especially organic polymers, exhibit a low vapor pressure and hence low volatility, possess a high migration stability, are stable toward thermal decomposition and exposure to acid, and possess a stabilization life which is improved over that of the compounds from the prior art.

For the purposes of this invention, expressions of the form $C_a$-$C_b$ identify chemical compounds or substituents having a particular number of carbon atoms. The number of carbon atoms can be selected from the entire range from a to b, including a and b; a is at least 1 and b is always greater than a. The chemical compounds or the substituents are further specified by expressions of the form $C_a$-$C_b$-V. V here is a chemical class of compound or of substituent, representing, for example, alkyl compounds or alkyl substituents.

Halogen is fluorine, chlorine, bromine or iodine, preferably fluorine, chlorine or bromine, more preferably fluorine or chlorine.

The collective terms indicated for the various substituents have the following particular definition:

$C_1$-$C_{20}$-Alkyl: straight-chain or branched hydrocarbon radicals having up to 20 carbon atoms, examples being $C_1$-$C_{10}$-alkyl or $C_{11}$-$C_{20}$-alkyl, preferably $C_1$-$C_{10}$-alkyl e.g., $C_1$-$C_3$-alkyl, such as methyl, ethyl, propyl, isopropyl, or $C_{4a}$-$C_6$-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, or $C_7$-$C_{10}$-alkyl, such as heptyl, octyl, 2-ethylhexyl, 2,4,4-trimethylpentyl, 1,1,3,3-tetramethylbutyl, nonyl or decyl, and also their isomers.

$C_3$-$C_{15}$-Cycloalkyl: monocyclic, saturated hydrocarbon groups having 3 up to 15 carbon ring members, preferably $C_3$-$C_8$-cycloalkyl such as cyclopropyl, cyclobutyl, cyclopentyl, cyclohexyl, cycloheptyl or cyclooctyl, and also a saturated or unsaturated polycyclic system such as norbornyl or norbenyl, for example. Particularly preferred is $C_5$-$C_6$-cycloalkyl.

$C_2$-$C_{20}$-Alkenyl: unsaturated, straight-chain or branched hydrocarbon radicals having 2 to 20 carbon atoms and at least one double bond, preferably one double bond, in any position, examples being $C_2$-$C_{10}$-alkenyl or $C_{11}$-$C_{20}$-alkenyl, preferably $C_2$-$C_{10}$-alkenyl such as $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, or $C_5$-$C_6$-alkenyl, such as 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, and also $C_7$-$C_{10}$-alkenyl, such as the isomers of heptenyl, octenyl, nonenyl or decenyl.

$C_1$-$C_{20}$-Alkylene: straight-chain or branched hydrocarbon radicals having two free valences having 1 to 20 carbon atoms, examples being $C_1$-$C_{10}$-alkylene or $C_{11}$-$C_{20}$-alkylene, preferably $C_1$-$C_{10}$-alkylene, especially methylene, dimethylene, trimethylene, tetramethylene, pentamethylene or hexamethylene.

$C_2$-$C_{20}$-Alkenylene: $C_2$-$C_{20}$-alkenyl as described above having two free valences.

$C_3$-$C_{12}$-Alkynoyl: a straight-chain or branched alkynyl group having 3 to 20 carbon atoms which is attached via a carbonyl group (—CO—) and comprises at least one triple C—C bond. Preference is given to $C_3$-$C_{10}$-alkynoyl, e.g., propynoyl, 2-butynoyl, 3-butynoyl.

$C_2$-$C_{20}$-Diacyl: a straight-chain or branched alkyl group having 2 to 20 carbon atoms which is attached via two carbonyl groups (—CO—). Preference is given to $C_2$-$C_{10}$-diacyl, e.g., oxalyl, malonyl, succinyl, glutaryl, sebacoyl.

$C_4$-$C_{20}$-Triacyl: a branched alkyl group having 4 to 20 carbon atoms which is attached via three carbonyl groups (—CO—). Preference is given to $C_4$-$C_{10}$-triacyl, e.g., 1,2,3-propanetricarbonyl.

$C_5$-$C_{20}$-Tetracyl: a branched alkyl group having 5 to 20 carbon atoms which is attached via four carbonyl groups (—CO—). Preference is given to $C_5$-$C_{10}$-tetracyl, e.g., methanetetracarbonyl or 1,2,3,4-butanetetracarbonyl.

$C_1$-$C_{21}$-Alkanoyl: a hydrogen atom or a straight-chain or branched alkyl group having 1 to 20 carbon atoms (as specified above) which is attached via one carbonyl group (—CO—), preferably $C_1$-$C_{13}$-alkanoyl such as, for example, formyl, acetyl, n- or isopropionyl, n-, iso-, sec- or tert-butanoyl, n-, iso-, sec- or tert-pentanoyl, n- or iso-nonanoyl, n-dodecanoyl.

Aryl: a mono- to tricyclic aromatic ring system comprising 6 to 14 carbon ring members, e.g. phenyl, naphthyl or anthracenyl, preferably a mono- to bicyclic, more preferably a monocyclic aromatic ring system.

Arylene: aryl having two free valences, a further hydrogen atom being absent from the aromatic ring system relative to the associated aryl; for example, phenylene, naphthylene.

Arylalkyl is a mono- to tricyclic aromatic ring system (as specified above) which is attached via a $C_1$-$C_{20}$-alkylene group, preferably a mono- to bicylic, more preferably a monocyclic aromatic ring system.

Heterocycles: five- to twelve-membered, preferably five- to nine-membered, more preferably five- to six-membered ring systems, comprising oxygen, nitrogen and/or sulfur atoms, optionally having two or more rings and/or being substituted, such as furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl.

$C_1$-$C_{20}$-Alkoxy is a straight-chain or branched alkyl group having 1 to 20 carbon atoms (as specified above) which is attached via an oxygen atom (—O—), examples being $C_1$-$C_{10}$-alkoxy or $C_{11}$-$C_{20}$-alkoxy, preferably $C_1$-$C_{10}$-alkyloxy, more preferably $C_1$-$C_3$-alkoxy, such as methoxy, ethoxy, propoxy, for example.

$C_4$-$C_{22}$-Alkoxyalkyl: a straight-chain or branched alkyl chain having 4 to 22 carbon atoms which is interrupted by an oxygen atom. Preference is given to those chains which comprise at least two carbon atoms both in front of and behind the oxygen atom.

Heteroatoms are preferably oxygen, nitrogen, sulfur or phosphorus. Any free valences of the heteroatoms are satisfied by hydrogen atoms.

In the context of the inventive use, preference is given to using sterically hindered amines comprising one or more groups of the general formula (I) where $R^1$ and $R^2$, each independently, alike or different, are H, $C_1$-$C_{20}$-alkyl or aryl; more preferably $R^1$ and $R^2$ each independently, alike or different, are H or $C_1$-$C_{20}$-alkyl, and in particular $R^1$ and $R^2$ are both H.

In the context of the inventive uses of sterically hindered amines, additional preference is given to using compounds of the general formulae (I-a) to (I-t):

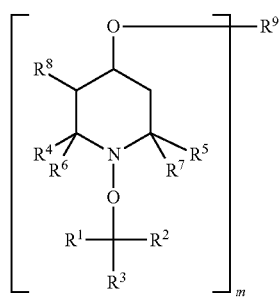
(I-a)

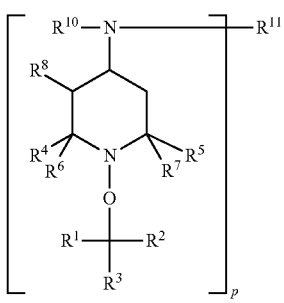
(I-b)

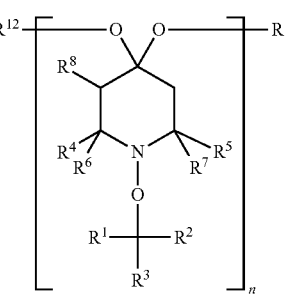
(I-c)

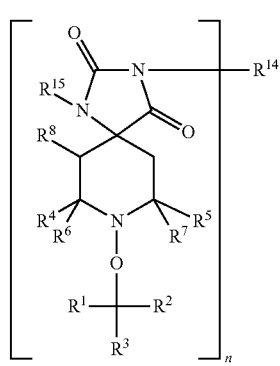
(I-d)

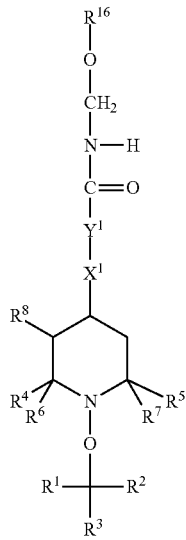
(I-e)

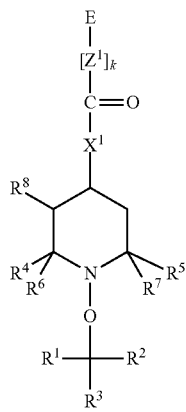
(I-f)

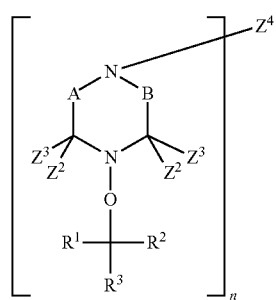
(I-g)

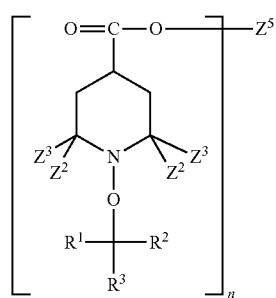
(I-h)

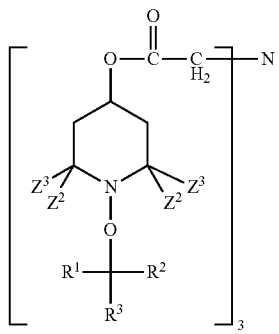
(I-i)
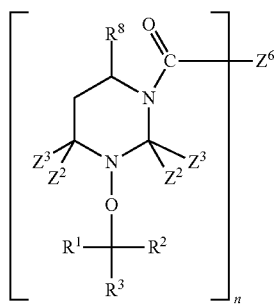
(I-j)
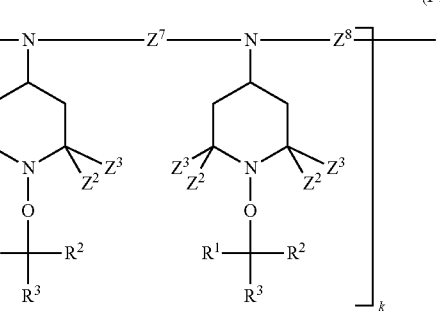
(I-k)
The end groups of the compound (I-k) here are arbitrary and of minor importance. Examples of suitable end groups include H, OH, $C_1$-$C_{20}$-alkyl, aryl, $C_1$-$C_{20}$-alkoxy, or $C_2$-$C_{20}$-alkenyl.
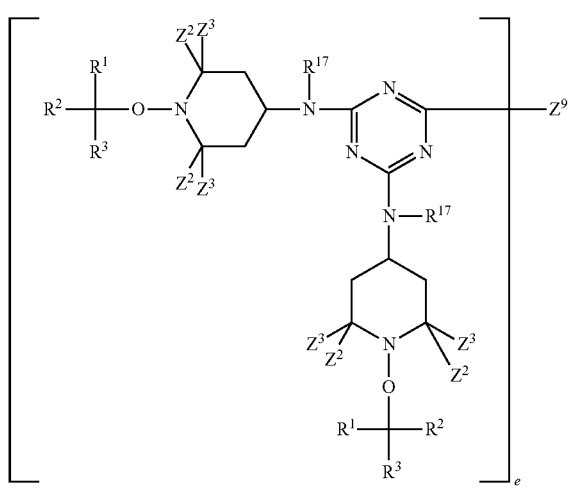
(I-l)
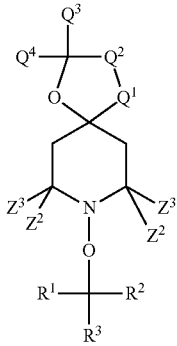
(I-m)
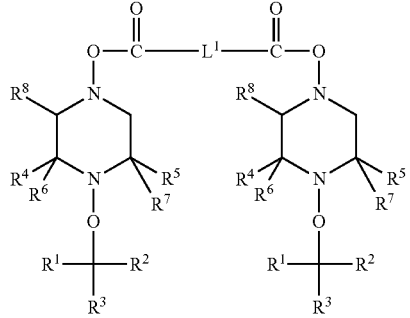
(I-n)
(I-o)—condensation product of (I-m) with epichlorohydrin (symbolic):
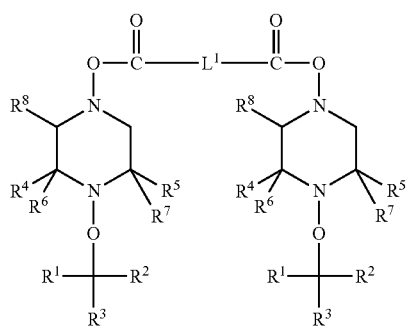
preferably:
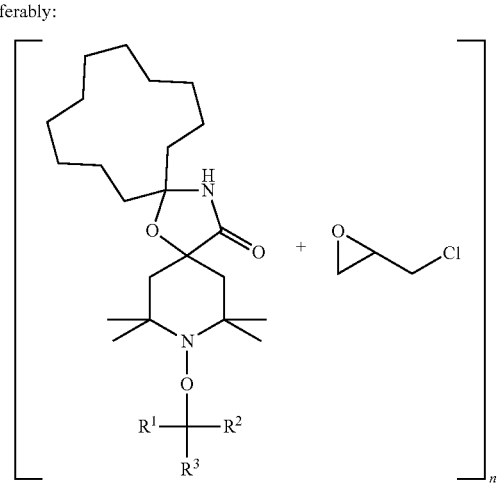

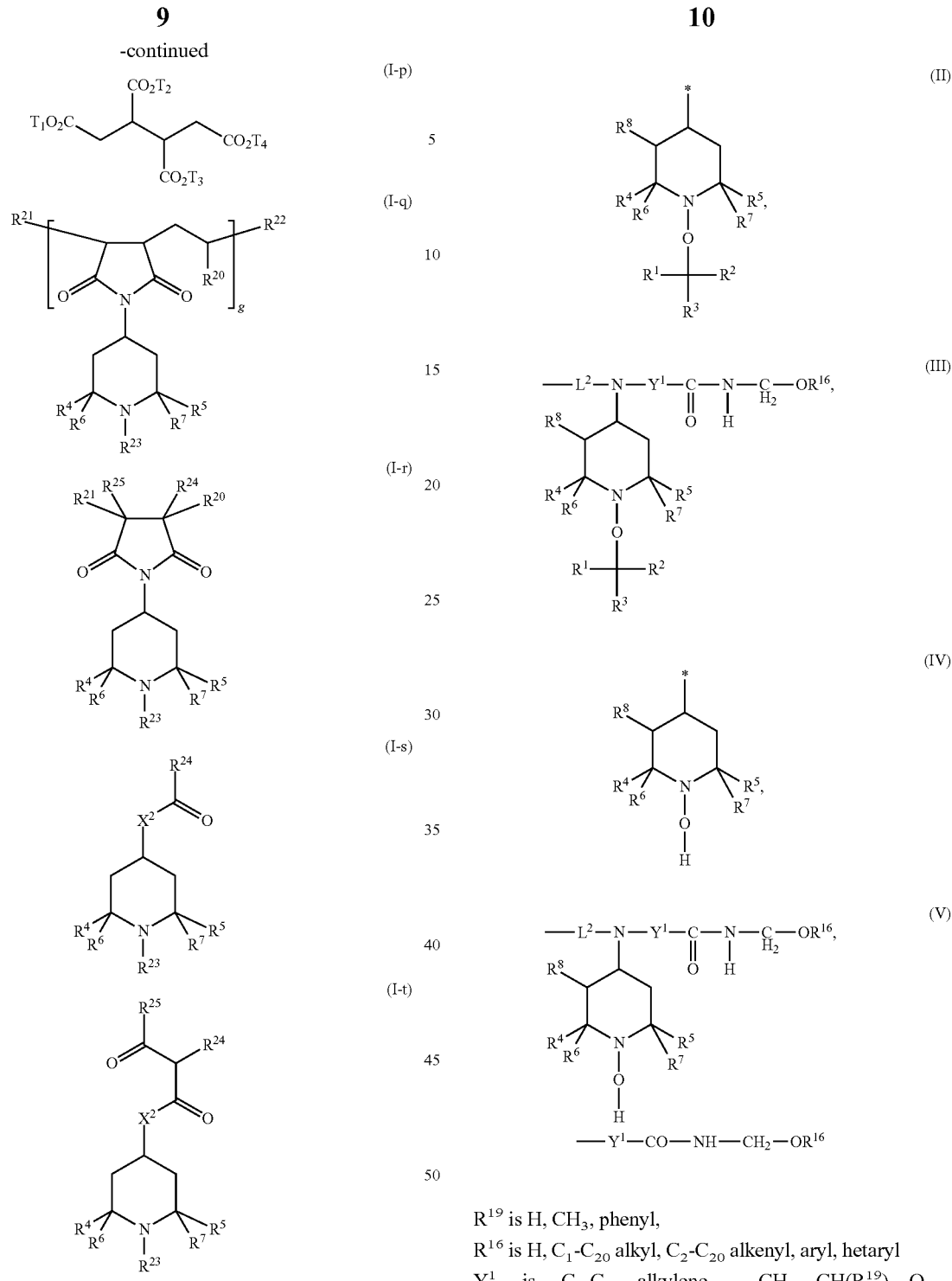

where $R^1$ to $R^7$ are as defined in claim 1,
and where
$R^8$ is H, $CH_3$,
$R^{10}$ is H, $C_1$-$C_{20}$ alkyl, $C_3$-$C_{15}$ cycloalkyl, $C_7$-$C_9$ aralkyl, $C_1$-$C_{21}$ alkanoyl, benzoyl,
$R^{15}$ is H, $C_1$-$C_{20}$ alkyl, allyl, benzyl, glycidyl, $C_1$-$C_{20}$ alkoxyalkyl,
$X^1$ is —N($R^{18}$)—, —O—,
$R^{18}$ is H, $C_1$-$C_{20}$ alkyl, $C_3$-$C_{15}$ cycloalkyl, $C_7$-$C_{12}$ aralkyl, cyanoethyl, aryl, —$CH_2$—CH($R^{19}$)—OH, a group of the general formula (II), (III), (IV) or (V), $R^{19}$ is H, $CH_3$, phenyl,
$R^{16}$ is H, $C_1$-$C_{20}$ alkyl, $C_2$-$C_{20}$ alkenyl, aryl, hetaryl
$Y^1$ is $C_1$-$C_3$ alkylene, —$CH_2$—CH($R^{19}$)—O—, —($CH_2$)$_3$—NH—, single bond,
$L^2$ is $C_2$-$C_6$ alkylene, arylene,
A, B each independently, alike or different, are methylene, carbonyl,
m is 1, 2, 3, 4,
and
if m is 1,
$R^9$ is H, $C_1$-$C_{20}$ alkyl, $C^2$-$C_{20}$ alkenyl, aryl, $C_7$-$C_{20}$ aralkyl, glycidyl, $C_2$-$C_{22}$ alkanoyl, a group of the general formula (VI) or (VII)

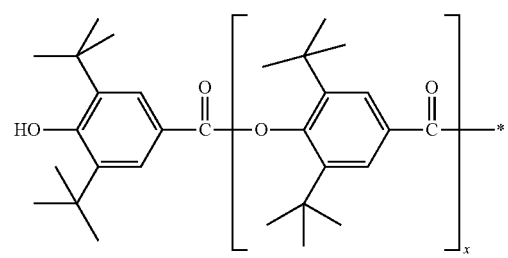

(VI)

x = 0, 1

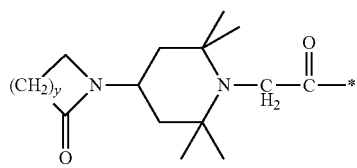

(VII)

y = 2, 3, 4 and
if m is 2,
$R^9$ is $C_1$-$C_{20}$ alkylene, $C_2$-$C_{20}$ alkenylene, xylylene, $C_2$-$C_{20}$ di-acyl, a group of the general formula (VIII) or (IX)

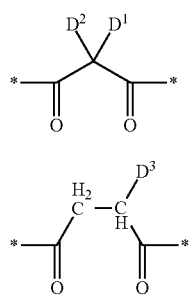

$D^1$ and $D^2$ each independently, alike or different, are H, $C_1$-$C_{20}$ alkyl, phenyl, benzyl, 3,5-di-tert-butyl-4-hydroxybenzyl or $D^1$ and $D^2$ together are $C_3$-$C_6$ alkylene, $D^3$ is $C_1$-$C_{20}$ alkyl, $C_2$-$C_{20}$ alkenyl,
and
if m is 3,
$R^9$ is $C_4$-$C_{20}$-tri-acyl,
and
if m is 4,
$R^9$ is $C_5$-$C_{20}$-tetra-acyl,
p is 1, 2, 3,
and
if p is 1,
$R^{11}$ is H, $C_1$-$C_{20}$ alkyl, $C_3$-$C_{15}$ cycloalkyl, $C_2$-$C_{20}$ alkenyl, $C_1$-$C_{21}$ alkanoyl, carbonyl, carbamide, aryl, $C_7$-$C_{10}$ aralkyl, glycidyl, —$CH_2$—$CH(OH)$—H, —$CH_2$—$CH(OH)$—$CH_3$, —$CH_2$—$CH(OH)$-phenyl, a group of the general formula (II) or (IV), or $R^{10}$ and $R^{11}$ together form a $C_4$-$C_6$ alkylene or 1-oxoalkylene, or a $C_2$-$C_{20}$ di-alkanoyl
and
if p is 2,
$R^{11}$ is $C_1$-$C_{12}$ alkylene, xylylene, —$CH_2$—$CH(OH)$—$CH_2$—, O—($C_2$-$C_{10}$ alkylene)—O—$CH_2$—$CH(OH)$—$CH_2$—, arylene, $C_6$-$C_{12}$ cycloalkylene, with the proviso that $R^{10}$ is not an alkynoyl, alkenoyl or benzoyl, $R^{11}$ can also be a $C_2$-$C_{20}$ di-acyl, or is —CO—, a group of the general formula (X)

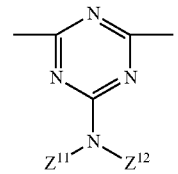

(X)

where $Z^{11}$ and $Z^{12}$ each independently are, H, $C_1$-$C_{20}$ alkyl, a group of the general formula (II), or $Z^{11}$ and $Z^{12}$ together form $C_4$-$C_6$ alkylene or 3-oxapentamethylene,
and
if p is 3,
$R^{11}$ is 2,4,6-triazinetriyl,
n is 1, 2
and
if n is 1,
$R^{12}$ is $C_1$-$C_{20}$ alkyl, $C_2$-$C_{20}$ alkenyl, $C_7$-$C_{12}$ aralkyl,
$R^{13}$ is H, $C_1$-$C_{20}$ alkyl, $C_2$-$C_{20}$ alkenyl, $C_7$-$C_{12}$ aralkyl, or $R^{13}$ together with $R^{12}$ forms a $C_2$-$C_8$ alkylene, $C_2$-$C_8$-hydroxyalkylene, $C_4$-$C_{22}$-acyloxyalkylene,
$R^{14}$ is H, $C_1$-$C_{20}$ alkyl, $C_3$-$C_5$ alkenyl, $C_7$-$C_9$ aralkyl, $C_3$-$C_{15}$ cycloalkyl, $C_2$-$C_4$ hydroxyalkyl, $C_2$-$C_6$ alkoxyalkyl, aryl, glycidyl, —$(CH_2)_t$—COO—Q, —$(CH_2)_t$—O—CO—Q, where t is 1, 2 and Q is $C_1$-$C_4$ alkyl, phenyl,
and
if n is 2,
$R^{12}$, $R^{13}$ are (—$CH_2$)$_2$C($CH_2$—)$_2$,
$R^{14}$ is $C_2$-$C_{20}$ alkylene, arylene, —$CH_2CH(OH)$—$CH_2$—O—X—$CH_2$—$CH(OH)$—$CH_2$—, where X is $C_2$-$C_{10}$ alkylene, arylene, $C_6$-$C_{12}$ cycloalkylene, or —$CH_2CH(OZ')$—$CH_2$—(O—$CH_2$—$CH(OZ')CH_2$)$_2$, where Z' is H, $C_1$-$C_{20}$ alkyl, allyl, benzyl, $C_2$-$C_{12}$ alkynoyl, benzoyl,
$Z^1$ is ethylene, 1,2-propylene, repeating unit of a polymer or copolymer derived from one or more alpha-olefins,
k is an integer from the range from 2 to 100,
E is H, $C_1$-$C_{20}$ alkyl, aryl, alkoxy, $C_2$-$C_{20}$ alkenyl,
$Z^4$ has the same definition as $R^{11}$ when p is 1 or 2,
$Z^2$ is methyl,
$Z^3$ is methyl, ethyl, or $Z^3$ and $Z^2$ together form a tetramethylene or pentamethylene group,
$Z^5$ has the same definition as $R^{14}$,
$Z^7$ and $Z^8$ each independently, alike or different, are $C_2$-$C_{12}$-alkylene, or $Z^7$ is a group of the general formula (VIII),
e is 2, 3, 4,
$Z^9$ is —$N(R^{13})$—$(CH_2)_d$—$N(R^{13})$—, or a group of the general formula (XI)

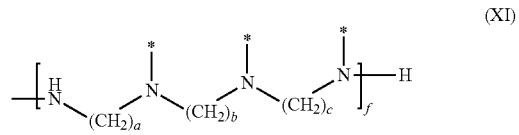

(XI)

where a, b, c each independently, alike or different, are 2 or 3
and d is an integer from the range from 2 to 10,
and f is 0 or 1, $R^{17}$ has the same definition as $R^{10}$, $Z^6$ has the same definition as $R^{11}$, $Q^1$ and $Q^2$ different from one another, are each —CO—, $N(Q^5)$—

$Q^5$ is H, $C_1$-$C_{20}$ alkyl, $C_4$-$C_{20}$ alkoxycarbonyl, $Q^3$ is H, $C_1$-$C_{20}$ alkyl, phenyl, naphthyl, $Q^4$ (is H, $C_1$-$C_{20}$-alkyl, phenyl, naphthyl, $C_7$-$C_{12}$ phenylalkyl, or $Q^4$ and $Q^3$ together form a $C_4$-$C_{17}$ alkylene L1 is single bond, $C_1$-$C_{12}$ alkylene, phenylene —NH—($C_1$-$C_{12}$-alkylene)-NH—

$T^1, T^2, T^3, T^4$ each independently, alike or different are $C_2$-$C_{20}$ alkyl, or a structural element of the general formula (II), with the proviso that at least one of the substituents $T^1$, $T^2$, $T^3$ or $T^4$ corresponds to a structural element of the general formula (II)

g is an integer from the range from 2 to 1000, $R^{20}$ is $C_1$-$C_{30}$ alkyl, aryl, mixture of different $C_1$-$C_{30}$ alkyls, $R^{21}$ and $R^{22}$ each independently, alike or different, are H, $C_1$-$C_{20}$ alkyl, aryl, $C_1$-$C_{20}$ alkoxy, $C_2$-$C_{20}$ alkenyl, $R^{23}$ is H, O, OH, $C_1$-$C_{20}$ alkyl, —OC($R^1R^2R^3$), with the proviso that at least one of the substituents $R^{23}$ is —OC($R^1R^2R^3$), $R^{24}$ and $R^{25}$ each independently, alike or different, are $C_1$-$C_{24}$ alkyl, preferably $C_{10}$-$C_{24}$ alkyl, more preferably $C_{14}$-$C_{22}$ alkyl, very preferably $C_{18}$-$C_{22}$-alkyl, $X^2$ is O, NH and where $R^9$, $R^{11}$, $Q^3$, and $Q^4$ may each be interrupted at any position by one or more heteroatoms, the number of these heteroatoms being not more than 10, preferably not more than 8, very preferably not more than 5 and in particular not more than 3, and/or may each be substituted at any position, but not more than five times, preferably not more than four times and more preferably not more than three times, by $C_1$-$C_{20}$ alkyl, $C_1$-$C_{20}$ alkoxy, aryl, a heterocycle, heteroatoms or halogen, which may likewise be substituted at most two times, preferably at most one time, by the stated groups.

It will be appreciated that in the context of the inventive use it is also possible to use mixtures of sterically hindered amines of the formulae (I-a) to (I-t).

Particular preference is given, in the context of the inventive uses of sterically hindered amines, to using compounds of the general formulae I-a, I-b, I-k, I-l, I-m, I-o, I-p and I-q. Especially preferred are sterically hindered amine compounds of the general formulae I-b and I-q.

In a further preferred embodiment of the inventive use the substituents $R^4$, $R^5$, $R^6$ and $R^7$ in the formulae (I) and also (I-a) to (I-t) all have the definition of a methyl group.

In a further preferred embodiment of the inventive use the substituent $R^8$ in the formulae (I-a) to (I-t) is a hydrogen atom.

In a further particularly preferred embodiment of the inventive use the substituents $R^4$, $R^5$, $R^6$, and $R^7$ in the formulae (I-a) to (I-t) alt have the definition of a methyl group and the substituent $R^8$ is a hydrogen atom.

In a further preferred embodiment of the inventive use the sterically hindered amine corresponds to the formulae (I-a) and $R^4$, $R^5$, $R^6$, and $R^7$ are all methyl, $R^8$ is hydrogen, m is 1, and $R^9$ is a mixture of $C_{12}$-$C_{21}$-alkanoyls, in particular a mixture of $C_{12}$-$C_{21}$-alkanoyls composed mostly of $C_{17}$-$C_{19}$-alkanoyls.

In another preferred embodiment of the inventive use the sterically hindered amine corresponds to the formula (I-a) and $R^4$, $R^5$, $R^6$, and $R^7$ are all methyl, $R^8$ is hydrogen, m is 2, and $R^9$ is $C_{10}$-diacyl.

In another preferred embodiment of the inventive use the sterically hindered amine corresponds to the formula (I-b) and $R^4$, $R^5$, $R^6$, and $R^7$ are all methyl, $R^8$ is hydrogen, $R^{19}$ is formyl, p is 2, and $R^{11}$ is hexamethylene.

In another preferred embodiment of the inventive use the sterically hindered amine corresponds to the formula (I-k) and $Z^2$ and $Z^3$ are both methyl, $Z^7$ is a group of the general formula (X), $Z^{11}$ is hydrogen, $Z^{12}$ is tert-octyl, and $Z^8$ is hexamethylene. The end groups of the chain are a result of the preparation conditions. For example, the chains are substituted at the end by H or OH.

In another preferred embodiment of the inventive use the sterically hindered amine corresponds to the formula (I-k) and $Z^2$ and $Z^3$ are both methyl, $Z^7$ is a group of the general formula (X), $Z^{11}$ is n-butyl, $Z^{12}$ is a group of the general formula (II), and $Z^8$ is hexamethylene, and $R^4$, $R^5$, $R^6$, and $R^7$ are all methyl. The end groups of the chain are a result of the preparation conditions. For example, the chains are substituted at the end by H or OH.

In another preferred embodiment of the inventive use the sterically hindered amine corresponds to the formula (I-l) and $Z^2$ and $Z^3$ are both methyl, $R^{17}$ is n-butyl, e is 4, $Z^9$ is a group of the general formula (XI), and a is 3, c is 3, b is 2, and f is 1.

In another preferred embodiment of the inventive use the sterically hindered amine corresponds to the formula (I-m) and $Z^2$ and $Z^3$ are both methyl, $Q^3$ and $Q^4$ together form a $C_{11}$-alkylene, and $Q^1$ is C=O and $Q^2$ is N—H.

In another preferred embodiment of the inventive use the sterically hindered amine corresponds to the formula (I-o) and $Z^2$ and $Z^3$ are both methyl, $Q^3$ and $Q^4$ together form a $C_{11}$-alkylene, and $Q^1$ is C=O and $Q^2$ is N—H.

In another preferred embodiment of the inventive use the sterically hindered amine corresponds to the formula (I-p) and $T^1$, $T^2$, $T^3$, and $T^4$ are all a group of the general formula (II), $R^4$, $R^5$, $R^6$, and $R^7$ are all methyl, and $R^8$ is hydrogen.

In another preferred embodiment of the inventive use the sterically hindered amine corresponds to the formula (I-p), with $T^1$, $T^2$, $T^3$, and $T^4$ being $C_{13}$-alkyl, or a mixture of $C_{13}$-alkyls, or a group of the general formula (II), where $R^4$, $R^5$, $R^6$, and $R^7$ are all methyl and $R^8$ is hydrogen.

In another preferred embodiment of the inventive use the sterically hindered amine corresponds to the formula (I-q) where $R^{20}$ is a mixture of $C_{18}$-$C_{22}$-alkyl groups, in particular a mixture of $C_{18}$-alkyl, $C_{20}$-alkyl, and $C_{22}$-alkyl. Particular preference is given here to steric amines of the formula (I-q) for which $R^{20}$ is a mixture of $C_{18}$-$C_{22}$-alkyl groups, in particular a mixture of $C_{18}$-alkyl, $C_{20}$-alkyl, and $C_{22}$-alkyl, and the majority (more than 50%) of the substituents $R^{23}$ correspond to a group —OC$R^1R^2R^3$.

Sterically hindered amines comprising one or more groups of the general formula (I) and sterically hindered amines of the formula (I-a) to (I-t) can be prepared in accordance with the process known to the skilled worker. These compounds are prepared in general by oxidizing the corresponding N—H derivatives with a suitable peroxy compound, examples being hydrogen peroxide or tert-butyl peroxide, in the presence of a metal carbonyl or metal oxide catalyst, and then reducing the oxyl compound to the corresponding N—OH derivative, in particular by catalytic hydrogenation. The N—OH derivatives can then be alkylated using sodium hydride and halogenated hydrocarbons or their derivatives, benzyl bromide, for example (Entezami et al., Polym. Adv. Technol. 2007, 18, 306-312).

An alternative option is to carry out coupling of nitroxyl radicals with hydrocarbon radicals, the hydrocarbon radicals, or derivatives thereof, being generated by thermal decomposition of di-tert-butyl peroxide in the presence of the hydrocarbons, in the presence of toluene or ethylbenzene, for example (Hawker et al., Macromolecules 1996, 29, 5245).

Another process for preparing sterically hindered amines comprising one or more groups of the general formula (I) and sterically hindered amines of the formula (I-a) to (I-t) starts directly from the N—H derivatives and comprises the oxidation steps and alkylation steps in a single process step without the isolation of the N—OH or nitroxyl radical derivatives (WO 2008/003602 A1).

The N—H derivatives are frequently available commercially as starting products or can be prepared by means of methods known to the skilled worker, as described for example in EP 0 316 582 A1, EP 0 316 582 A, WO 94/12544.

In one preferred embodiment of the inventive use the stabilized inanimate organic materials are plastics or coating materials, especially plastics. More preferably these plastics are agricultural films, especially glasshouse films, preferably comprising polyethylene. Further preferred plastics are PVC or flame-retarded thermoplastics, especially flame-retarded polypropylene, ABS or polystyrene.

Further plastics or polymers which can be stabilized as inanimate organic materials include, for example the following:

Polymers of mono- and diolefins, such as, for example, low or high density polyethylene, linear polybut-1-ene, polyisoprene, polybutanes, and also copolymers or mono- or diolefins or mixtures of the stated polymers;

Copolymers of mono- or diolefins with other vinyl monomers, such as, for example, ethylene alkyl acrylate copolymers, ethylene-alkyl methacrylate copolymers, ethylene-vinyl acetate copolymers or ethylene-acrylic acid copolymers;

Polystyrene;

Copolymers of styrene or alpha-methylstyrene with dienes or acrylic derivatives, such as, for example, styrene-butadiene, styrene-acrylonitrile, styrene-ethyl methacrylate, styrene-butadiene-ethyl acrylate, styrene-acrylonitrile-methacrylate;

ABS, MBS or similar polymers;

Halogenated polymers, such as polyvinyl chloride, polyvinyl fluoride, polyvinylidene fluoride, and their copolymers;

Polymers derived from alpha,beta-unsaturated acids and derivatives thereof, such as polyacrylates, polymethacrylates, polyacrylamides, and polyacrylonitriles;

Polymers deriving from unsaturated alcohols and amines and/or from their acrylic derivatives or acetals, e.g., polyvinyl alcohol and polyvinyl acetate;

Polyurethanes, polyamides, polyurea, polyesters, polycarbonates, polysulfones, polyethersulfones, and polyetherketones.

Furthermore it is possible, in accordance with the inventive use, optionally with addition of one or more antioxidants, to carry out stabilization, in accordance with the invention, of coating materials, especially those coating materials and coating systems which are subject to a high degree to exposure to environmental influences, such as sunlight and heat. These are, for example, coating materials for exterior coatings, industrial coatings or vehicle finishes. Additionally these are coating materials for baking finishes, especially in the automobile sector.

The sterically hindered amines can be added in solid or dissolved form to the coating material. Their solubility in coating systems, which is generally good, is of particular advantage in this context.

The sterically hindered amines comprising one or more groups of the general formula (I), in particular sterically hindered amines of the formula (I-a) to (I-t), are used preferably to stabilize polyolefins, especially ethylene polymers or propylene polymers, polyurethanes, and polyamides.

The sterically hindered amines comprising one or more groups of the general formula (I), in particular sterically hindered amines of the formula (I-a) to (I-t), are added to the inanimate organic material to be stabilized, in particular to the plastics to be stabilized, in an amount of 0.01 to 5% by weight, preferably of 0.02 to 1% by weight, based on the inanimate organic material. Where the inanimate organic material is composed of relatively small molecules, such as in the case, for instance, of the production of plastics from the corresponding monomers, the addition may be made before, during or after the synthesis of the organic material.

For mixing the sterically hindered amines and, optionally, further additives, listed below, with the organic material, in particular with the plastics and coating materials, it is possible to employ all known apparatus and methods for mixing stabilizing materials or other additives into organic materials, polymers, for example.

By way of example the sterically hindered amines and, optionally, other additives may be readily incorporated into the polymer by conventional techniques at any desired stage before the production of the moldings formed from the polymer. For example, they can be mixed with the polymer in dry powder form, or a suspension or emulsion of the stabilizer can be mixed with a solution, suspension or emulsion of the polymer. The sterically hindered amines can be added individually or in a mixture with one another. Optionally, the individual components can be mixed with one another, in the course of melting (melt mixing) prior to incorporation into the material to be stabilized. The sterically hindered amines and also, optionally, further additives may additionally be added to this material to be stabilized in the form of a premix comprising these components in a concentration of, for example, about 2.5 to about 25% by weight. In the course of these operations it is possible to employ the polymer in the form of powders, granules, solutions, suspensions or latices. Mixing may be carried out before or during the shaping operation. Elastomers may be stabilized in the form of latices.

Another possibility for incorporating stabilizers of the invention into polymers is to add them before, during or directly after the polymerization of the corresponding monomers. If added before or during the polymerization, the stabilizers of the invention may also act as chain-length regulators of the polymers (chain terminators).

In a further preferred embodiment of the inventive use it is possible, in addition to the sterically hindered amines, for further additives to be employed additionally, examples being UV absorbers, antioxidants, costabilizers, metal deactivators, metal soaps, plasticizers, antistats, lubricants, release agents, processing assistants, antiblocking agents, antifogging agents, flame retardants, pigments, dyes, IR radiation regulator compounds, foaming agents, nucleating agents, and fillers.

The inanimate organic material, more particularly plastics and coating materials, stabilized by the sterically hindered amines comprising one or more groups of the general formula (I), especially sterically hindered amines of the formula (I-a) to (I-t), may therefore, optionally, comprise further additives as well, examples being UV absorbers, antioxidants, costabilizers, metal deactivators, metal soaps, plasticizers, antistats, lubricants, release agents, processing assistants, antiblocking agents, antifogging agents, flame retardants, pigments, dyes, IR radiation regulator compounds, foaming agents, nucleating agents, and fillers. Selectively, for example, at least one or more further additives a) to t) are used:

a) 4,4-diarylbutadienes,
b) cinnamic esters,
c) benzotriazoles,
d) hydroxybenzophenones,
e) diphenylcyanoacrylates,
f) oxamides,
g) 2-phenyl-1,3,5-triazines,
h) antioxidants,
i) nickel compounds,
j) sterically hindered amines not comprising one or more groups of general formula (I),
k) metal deactivators,
l) phosphites and phosphonites,
m) hydroxylamines,
n) nitrones,
o) amine oxides,
p) benzofuranones and indolinones,
q) thiosynergists,
r) peroxide-destroying compounds,
s) basic costabilizers and/or
t) IR radiation regulator compounds.

Group a) of the 4,4-diarylbutadienes includes for example compounds of the formula (aa)

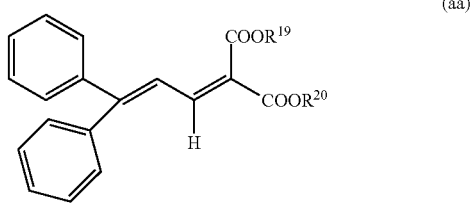

(aa)

The compounds are known from EP-A-916 335. The substituents $R^{19}$ and $R^{20}$, independently of one another, identically or differently, are preferably $C_1$-$C_8$ alkyl and $C_5$-$C_8$ cycloalkyl.

Group b) of the cinnamic esters includes for example 2-isoamyl 4-methoxycinnamate, 2-ethylhexyl 4-methoxycinnamate, methyl α-methoxycarbonylcinnamate, methyl α-cyano-β-methyl-p-methoxycinnamate, butyl α-cyano-β-methyl-p-methoxycinnamate, and methyl α-methoxycarbonyl-p-methoxycinnamate.

Group c) of the benzotriazoles includes for example 2-(2'-hydroxyphenyl)benzotriazoles such as 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the product of esterifying 2-[3'-tert-butyl-5'-(2-methoxycarbonylethyl)-2'-hydroxyphenyl]-2H-benzotriazole with polyethylene glycol 300; [R—CH2CH2-COO(CH2)3]2 where R=3'-tert-butyl-4'-hydroxy-5'-2H-benzotriazol-2-ylphenyl and mixtures thereof.

Group d) of the hydroxybenzophenones includes for example 2-hydroxybenzophenones such as 2-hydroxy-4-methoxybenzophenone, 2,2'-dihydroxy-4-methoxybenzophenone, 2,4-dihydroxybenzophenone, 2,2',4,4'-tetrahydroxybenzophenone, 2,2'-dihydroxy-4,4'-dimethoxybenzophenone, 2,2'-dihydroxy-4,4'-dimethoxybenzophenone, 2-hydroxy-4-(2-ethylhexyloxy)benzophenone, 2-hydroxy-4-(n-octyloxy)benzophenone, 2-hydroxy-4-methoxy-4'-methylbenzophenone, 2-hydroxy-3-carboxybenzophenone,2-hydroxy-4-methoxybenzophenone-5-sulfonic acid and its sodium salt, and 2,2'-dihydroxy-4,4'-dimethoxybenzophenone-5,5'-bissulfonic acid and its sodium salt.

Group e) of the diphenylcyanoacrylates includes for example ethyl 2-cyano-3,3-diphenylacrylate, obtainable commercially for example under the name Uvinul® 3035 from BASF SE, Ludwigshafen, 2-ethylhexyl 2-cyano-3,3-diphenylacrylate, obtainable commercially for example as Uvinul® 3039 from BASF SE, Ludwigshafen, and 1,3-bis[(2'-cyano-3',3'-diphenylacryloyl)oxy]-2,2-bis{[2'-cyano-3',3'-diphenylacryloyl)oxy]methyl}propane, obtainable commercially for example under the name Uvinul® 3030 from BASF SE, Ludwigshafen.

Group f) of the oxamides includes for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, and also mixtures of ortho-, para-methoxy-disubstituted oxanilides and mixtures of ortho- and para-ethoxy-disubstituted oxanilides.

Group g) of the 2-phenyl-1,3,5-triazines includes for example 2-(2-hydroxyphenyl)-1,3,5-triazines such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropoxy)phenyl]-4,6-bis(2,4-dimethyl)-1,3,5-triazine, 2-[4-(dodecyloxytridecyloxy-2-hydroxypropoxy)-2-hydroxyphenyl]-4,6-bis(2,4-dimethylphenyl) 1,3,5-triazine, 2-[2-hydroxy-4-(2-hydroxy-3-dodecyloxypropoxy)phenyl]-4,6-bis-(2,4-dimethylphenyl)-1,3,5-triazine, 2-(2-hydroxy-4-hexyloxyphenyl)-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, and 2-(2-hydroxyphenyl)-4-(4-methoxyphenyl)-6-phenyl-1,3,5-triazine.

Group h) of the antioxidants comprises, for example:
Alkylated monophenols such as, for example, 2,6-di-tert-butyl-4-methylphenol, 2-tert-butyl-4,6-dimethylphenol, 2,6- di-tert-butyl-4-ethylphenol, 2,6-di-tert-butyl-4-n-butyl-phenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, unbranched or sidechain-branched nonylphenols such as, for example, 2,6-dinonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol, and mixtures thereof.

Alkylthiomethylphenols such as, for example, 2,4-dioctylthiomethyl-6-tert-butylphenol, 2,4-dioctylthiomethyl-6-methylphenol, 2,4-dioctylthiomethyl-6-ethylphenol and 2,6-didodecylthiomethyl-4-nonylphenol.

Hydroquinones and alkylated hydroquinones such as, for example, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, and bis-(3,5-di-tert-butyl-4-hydroxyphenyl)adipate.

Tocopherols, such as, for example, α-tocopherol, β-tocopherol, γ-tocopherol, δ-tocopherol, and mixtures thereof (vitamin E).

Hydroxylated thiodiphenyl ethers such as, for example, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), and 4,4'-bis(2,6-dimethyl-4-hydroxyphenyl)disulfide.

Alkylidenebisphenols such as, for example, 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis-[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3-tert-butyl-4-hydroxyphenyl)butyrate], bis(3-tert-butyl-4-hydroxy-5-methylphenyl)dicyclopentadiene, bis[2-(3'-tert-butyl-2-hydroxy-5-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyl)pentane.

Benzyl compounds such as, for example, 3,5,3',5'-tetra-tert-butyl-4,4'-dihydroxy-dibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl-4-hydroxybenzyl)amine, 1,3,5-tri(3,5-di-tert-butyl-4-hydroxybenzyl)-2,4,6-trimethylbenzene, di(3,5-di-tert-butyl-4-hydroxybenzyl)sulfide, isooctyl 3,5-di-tert-butyl-4-hydroxybenzylmercapto-acetate, bis(4-tert-butyl-3-hydroxy-2,6-dimethylbenzyl)dithiol terephthalate, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 3,5-di-tert-butyl-4-hydroxybenzylphosphoric acid dioctadecyl ester, and 3,5-di-tert-butyl-4-hydroxybenzyl-phosphoric acid monoethyl ester, calcium salt.

Hydroxybenzylated malonates such as, for example, dioctadecyl 2,2-bis(3,5-di-tert-butyl-2-hydroxybenzyl)malonate, dioctadecyl-2-(3-tert-butyl-4-hydroxy-5-methylbenzyl)malonate, didodecyl mercaptoethyl-2,2-bis(3,5-di-tert-butyl-4-hydroxybenzyl)malonate, and bis[4-(1,1,3,3-tetramethylbutyl)phenyl] 2,2-bis(3,5-di-tert-butyl-4-hydroxybenzyl)malonate.

Hydroxybenzyl aromatics such as, for example, 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, and 2,4,6-tris(3,5-di-tert-butyl-4-hydroxybenzyl)phenol.

Triazine compounds such as, for example, 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, and 1,3,5-tris(3,5-dicyclohexyl-4-hydroxybenzyl)isocyanurate.

Benzylphosphonates such as, for example, dimethyl 2,5-di-tert-butyl-4-hydroxybenzylphosphonate, diethyl 3,5-di-tert-butyl-4-hydroxybenzylphosphonate(diethyl (3,5-bis(1,1-dimethylethyl)-4-hydroxyphenyl)methylphosphonate), dioctadecyl 3,5-di-tert-butyl-4-hydroxybenzylphosphonate, dioctadecyl 5-tert-butyl-4-hydroxy-3-methylbenzylphosphonate, and the calcium salt of monoethyl 3,5-di-tert-butyl-4-hydroxybenzylphosphonate.

Acylaminophenols such as, for example, 4-hydroxylauranilide, 4-hydroxystearanilide, 2,4-bisoctylmercapto-6-(3,5-tert-butyl-4-hydroxyanilino)-s-triazine, and octyl N-(3,5-di-tert-butyl-4-hydroxyphenyl)carbamate.

Esters of β-(3,5-di-tert-butyl-4-hydroxyphenyl)propionic acid with monohydric or polyhydric alcohols, such as with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, and 4-hydroxymethyl-1-phospha-2,6,7-trioxabicyclo[2.2.2]octane.

Esters of β-(5-tert-butyl-4-hydroxy-3-methylphenyl)propionic acid with monohydric or polyhydric alcohols, such as with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, and 4-hydroxymethyl-1-phospha-2,6,7-trioxabicyclo[2.2.2]octane.

Esters of β-(3,5-dicyclohexyl-4-hydroxyphenyl)propionic acid with monohydric or polyhydric alcohols, such as with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, and 4-hydroxymethyl-1-phospha-2,6,7-trioxabicyclo[2.2.2]octane.

Esters of 3,5-di-tert-butyl-4-hydroxyphenylacetic acid with monohydric or polyhydric alcohols, such as with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, and 4-hydroxymethyl-1-phospha-2,6,7-trioxabicyclo[2.2.2]octane.

Amides of β-(3,5-di-tert-butyl-4-hydroxyphenyl)propionic acid, such as N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (e.g., Naugard®XL-1 from Uniroyal).

Ascorbic Acid (Vitamin C)

Amine antioxidants, such as, for example, N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example, p,p'-di-tert-octyldiphenylamine, 4-n-butylaminophenol, 4-butyrylaminophenol, 4-nonanoyl-aminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane,1,2-bis(phenylamino)propane, o-tolyl biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperidin-4-yl)hexamethylenediamine, 2,2,6,6-tetramethylpiperidin-4-one, 2,2,6,6-tetramethylpiperidin-4-ol, the dimethyl succinate polymer with 4-hydroxy-2,2,6,6-tetramethyl-1-piperidineethanol [CAS number 65447-77-0], (for example, Tinuvin® 622 from Ciba Specialty Chemicals, Inc.), polymer of 2,2,4,4-tetramethyl-7-oxa-3,20-diazadispiro[5.1.11.2]heneicosan-21-one and epichlorohydrin [CAS No.: 202483-55-4], for example (Hostavin® N 30 from Clariant).

Group i) of the nickel compounds includes for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyl-diethanolamine, nickel dibutyl dithiocarbamate, nickel salts of 4-hydroxy-3,5-di-tert-butylbenzylphosphonic acid monoalkyl esters such as of the methyl or ethyl esters, for example, nickel complexes of ketoximes such as, for example, of 2-hydroxy-4-methylphenyl undecyl ketoxime, and the nickel complex of 1-phenyl-4-lauroyl-5-hydroxypyrazole, with or without additional ligands.

Group j) of the sterically hindered amines not comprising one or more groups of general formula (1), includes for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate(n-butyl-3,5-di-tert-butyl-4-hydroxybenzylmalonic acid bis(1,2,2,6,6-pentamethylpiperidyl)ester), condensation product of 1-(2-hydroxyethyl)-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl) 1,2,3,4-butanetetracarboxylate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensation products of N,N'-bis(2,2,6,6-tetramethyl-4-piperidyl)hexamethylenediamine and 4-morpholino-2,6-dichloro-1,3,5-triazine, condensation product of 2-chloro-4,6-bis(4-n-butylamino-2,2,6,6-tetramethylpiperidyl)-1,3,5-triazine and 1,2-bis(3-aminopropylamino)ethane, condensation product of 2-chloro-4,6-di-(4-n-butylamino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, mixture of 4-hexadecyloxy- and 4-stearyloxy-2,2,6,6-tetramethylpiperidine, condensation product of N,N'-bis-(2,2,6,6-tetramethyl-4-piperidyl)hexamethylenediamine and 4-cyclohexylamino-2,6-dichloro-1,3,5-triazine, condensation product of 1,2-bis(3-aminopropylamino)ethane and 2,4,6-trichloro-1,3,5-triazine and also 4-butylamino-2,2,6,6-tetramethylpiperidine (CAS Reg. No. [136504-96-6]); N-(2,2,6,6-tetramethyl-4-piperidyl)-n-dodecyl-succinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4.5]decane, reaction product of 7,7,9,9-tetramethyl-2-cycloundecyl-1-oxa-3,8-diaza-4-oxospiro[4.5]decane and epichlorohydrin, 1,1-bis(1,2,2,6,6-pentamethyl-4-piperidyloxycarbonyl)-2-(4-methoxyphenyl)ethene, diester of 4-methoxymethylenemalonic acid with 1,2,2,6,6-pentamethyl-4-hydroxypiperidine, poly[methylpropyl-3-oxo-4-(2,2,6,6-tetramethyl-4-piperidyl)]-siloxane, 1-(2-hydroxy-2-methylpropoxy)-4-octadecanoyloxy-2,2,6,6-tetramethylpiperidine, 1-(2-hydroxy-2-methylpropoxy)-4- hexadecanoyloxy-2, 2,6,6-tetramethylpiperidine, the reaction product of 1-oxyl-4-hydroxy-2,2,6,6-tetramethylpiperidine and a carbon radical of t-amyl alcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl)sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl)succinate, bis(1-(2-hydroxy-2-methylpropoxy)-2,2,6,6-tetramethylpiperidin-4-yl) glutarate, 2,4-bis{N[1-(2-hydroxy-2-methylpropoxy)-2,2,6,6-tetramethylpiperidin-4-yl]-N-butylamino}-6-(2-hydroxyethylamino)-s-triazine, hexahydro-2,6-bis(2,2,6,6-tetramethyl-4-piperidyl)-1H,4H,5H,8H-2,3a,4a,6,7a,8a-hexaazacyclopenta[def]fluorene-4,8-dione (e.g. Uvinul® 4049 from BASF SE, Ludwigshafen), poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]]) [CAS No. 71878-19-8], 1,3,5-triazine-2,4,6-triamine, N,N'''-[1,2-ethanediylbis[[4,6-bis[butyl(1,2,2,6,6-pentamethyl-4-piperidinyl)amino]-1,3,5-triazin-2-yl]imino]-3,1-propanediyl]]bis[N',N''-dibutyl-N',N''-bis(1,2,2,6,6-pentamethyl-4-piperidinyl) (CAS No. 106990-43-6) (e.g., Chimassorb 119 from Ciba Specialty Chemicals, Inc.).

Group k) of the metal deactivators includes for example N,N'-diphenyloxalamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl-bisphenyl hydrazide, N,N'-diacetyladipic dihydrazide, N,N'-bis(salicyloyl)oxalic dihydrazide, and N,N'-bis(salicyloyl)thiopropionyl dihydrazide.

Group l) of the phosphites and phosphonites includes for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, diisodecyloxy pentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylenediphosphonite, 6-isooctyloxy-2,4,8,10-tetra-tert-butyl-dibenzo[d,f][1,3,2]dioxaphosphepine, 6-fluoro-2,4,8,10-tetra-tert-butyl-12-methyldibenzo[d,g][1,3,2] dioxaphosphocine, bis(2,4-di-tert-butyl-6-methylphenyl) methyl phosphite, bis(2,4-di-tert-butyl-6-methylphenyl) ethyl phosphite, 2,2',2''-nitrilo-[triethyl tris(3,3',5,5'-tetra-tert-butyl-1,1'-biphenyl-2,2'-diyl)phosphite], and 2-ethylhexyl-(3,3',5,5'-tetra-tert-butyl-1,1'-biphenyl-2,2'-diyl)phosphite.

Group m) of the hydroxylamines includes for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecylhydroxylamine, and N,N-dialkylhydroxylamine from hydrogenated tallow fatty amines.

Group n) of the nitrones includes for example N-benzyl α-phenyl nitrone, N-ethyl α-methyl nitrone, N-octyl α-heptyl nitrone, N-lauryl α-undecyl nitrone, N-tetradecyl α-tridecyl nitrone, N-hexadecyl α-pentadecyl nitrone, N-octadecyl α-heptadecyl nitrone, N-hexadecyl α-heptadecyl nitrone, N-octadecyl α-pentadecyl nitrone, N-heptadecyl α-heptadecyl nitrone, N-octadecyl α-hexadecyl nitrone, N-methyl α-heptadecyl nitrone, and nitrones derived from N,N-dialkylhydroxylamines prepared from hydrogenated tallow fatty amines.

Group o) of the amine oxides includes for example amine oxide derivatives as described in U.S. Pat. Nos. 5,844,029 and 5,880,191, didecylmethylamine oxide, tridecylamine oxide, tridodecylamine oxide, and trihexadecylamine oxide.

Group p) of the benzofuranones and indolinones includes for example those described in U.S. Pat. Nos. 4,325,863; 4,338,244; 5,175,312; 5,216,052; 5,252,643; in DE-A-4316611; in DE-A-4316622; in DE-A-4316876; in EP-A-0589839 or EP-A-0591102, or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis [5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, Irganox HP-136 from Ciba Specialty Chemicals, and 3-(2,3-dimethylphenyl)-5,7-di-tert-butyl-benzofuran-2-one.

Group q) of the thiosynergists includes for example dilauryl thiodipropionate or distearyl thiodipropionate.

Group r) of the peroxide-destroying compounds includes for example esters of β-thiodipropionic acid, for example, the lauryl, stearyl, myristyl or tridecyl ester, mercaptobenzimidazole or the zinc salt of 2-mercaptobenzimidazole, zinc dibutyldithiocarbamate, dioctadecyl disulfide, and pentaerythritol tetrakis(β-dodecylmercapto)propionate.

Group s) of the basic costabilizers includes for example melamine, polyvinylpyrrolidone, dicyandiamide, triallylcyanurate, urea derivatives, hydrazine derivatives, amines, polyamides, polyurethanes, alkali metal and alkaline earth metal salts of higher fatty acids, for example, calcium stearate, zinc stearate, magnesium behenate, magnesium stearate, sodium ricinoleate, and potassium palmitate, antimony pyrocatecholate or zinc pyrocatecholate.

Group t) of the IR radiation regulator compounds includes IR absorbers, examples being organic or inorganic IR absorbers, such as antimony-tin oxide (ATO), indium-tin oxide (ITO), and Lumogen® IR 1050 from BASF SE. Group t) further includes additives transparent to IR radiation, such as perylene compounds, examples being Lumogen® black FK 4280 and 4281 from BASF SE. Group t) also includes compounds which reflect IR radiation, especially pigments comprising iron oxides and chromium oxides, an example being Sicopal® Black K 0095, especially for use in plastics, and pigments comprising perylenes, examples being Paliogen® Black S 0084 and 0086, especially for use in coating materials.

Suitable additives are also the customary additives, such as pigments, dyes, nucleating agents, fillers, reinforcing agents, antifogging agents, biocides, and antistats, for example.

Suitable pigments are inorganic pigments, examples being titanium dioxide in its three modifications—rutile, anatase or brookite; ultramarine blue, iron oxides, bismuth vanadates or carbon black, and also the class of the organic pigments, examples being compounds from the class of the phthalocyanines, perylenes, azo compounds, isoindolines, quinophthalones, diketopyrrolopyrroles, quinacridones, dioxazines, and indanthrones.

By dyes are meant all colorants which dissolve completely in the plastic used or are present in a molecularly disperse distribution and can therefore be used for the high-transparency, nonscattering coloring of polymers. Likewise regarded as dyes are organic compounds which exhibit a fluorescence in the visible part of the electromagnetic spectrum, such as fluorescent dyes.

Suitable nucleating agents include for example inorganic substances, examples being talc, metal oxides such as titanium dioxide or magnesium oxide, phosphates, carbonates or sulfates, preferably of alkaline earth metals; organic compounds such as monocarboxylic or polycarboxylic acids and also their salts, such as 4-tert-butylbenzoic acid, adipic acid, diphenylacetic acid, sodium succinate or sodium benzoate; and polymeric compounds, such as ionic copolymers ("ionomers"), for example.

Suitable fillers and reinforcing agents include for example calcium carbonate, silicates, talc, mica, kaolin, barium sulfate, metal oxides and metal hydroxides, carbon black, graphite, wood flour and flours or fibers of other natural products, and synthetic fibers. Further suitable examples of fibrous or pulverulent fillers include carbon or glass fibers in the form of glass fabrics, glass mats or filament glass rovings, chopped glass, glass beads, and wollastonite. Glass fibers can be incorporated either in the form of short glass fibers or in the form of continuous fibers (rovings).

Examples of suitable antistats include amine derivatives such as N,N-bis(hydroxyalkyl)alkylamines or -alkylenamines, polyethylene glycol esters and ethers, ethoxylated carboxylic esters and carboxamides, and glyceryl mono- and distearates, and also mixtures thereof.

The weight ratio of the sterically hindered amines comprising one or more groups of the general formula (I), especially sterically hindered amines of the formula (I-a) to (I-t), in relation to the total amount of additives, if additives are present, is generally from 100:1 to 2:1, preferably from 50:1 to 5:1, more preferably from 30:1 to 7:1, particular preference being given to a mixture in the weight ratio of approximately 10:1.

One particularly advantageous embodiment of the inventive use comprises, in addition to the use of sterically hindered amines comprising one or more groups of the general formula (I), especially sterically hindered amines of the formula (I-a) to (I-t), the use of flame retardants. The flame retardants are generally selected from the following: melamine-based flame retardants and/or ammonium polyphosphate, bis(hexachlorocyclopentadieno)cyclooctane, tris(2,3-dibromopropy)isocyanurate, ethylenebistetrabromophthalimide, 1,2,5,6,9,10-hexabromocyclododecane and/or ethane-1,2-bis(pentabromophenyl). The use of mixtures of different flame retardants is of course also possible.

Likewise it is possible to use halogenated flame retardants selected from the following compounds: organic, aromatic, halogenated compounds, such as halogenated benzenes, biphenyls, phenols, ethers or esters thereof, bisphenols, diphenyl oxides, aromatic carboxylic acids or polyacids, anhydrides, amides or imides thereof; organic, cycloaliphatic or polycycloaliphatic, halogenated compounds; and organic aliphatic, halogenated compounds, such as halogenated paraffins, oligomers or polymers, alkyl phosphates or alkyl isocyanurates. These components are known from the prior art: cf. U.S. Pat. No. 4,579,906 (e.g., column 3, lines 30-41), U.S. Pat. No. 5,393,812; cf. also Plastics Additives Handbook, ed. by H. Zweifel, 5th edition, Hanser Verlag, Munich 2001, pp. 681-698. The halogenated flame retardants may comprise, for example, a chlorinated or brominated compound, selected for example from the following compounds: chloroalkyl phosphate esters (ANTIBLAZE® AB-100, Albright & Wilson; FYROL® FR-2, Akzo Nobel), polybrominated diphenyl oxide (DE-60F, Great Lakes Corp.), decabromodiphenyl oxide (DBDPO; SAYTEX® 102E), tris[3-bromo-2,2-bis (brommethyl)propyl]phosphate (PB 370, FMC Corp.), bis(2, 3-dibromopropyl ether) of bisphenol A (PE68), brominated epoxy resin, ethylenebis(tetrabromophthalimide) (SAYTEX® BT-93), bis(hexachlorocyclopentadieno)cyclooctane (DECLORANE PLUS®), chlorinated paraffins, 1,2-bis(tribromophenoxy)ethane (FF680), tetrabromobisphenol A (SAYTEX® RB 100), ethylenebis(dibromonorbornane-dicarboximide) (SAYTEX® BN-451), bis(hexachlorocyclopentadieno)cyclooctane, tris-(2,3-dibromopropy)isocyanurate, ethylenebistetrabromophthalimide. Brominated flame retardants are preferred. Particularly preferred flame retardants are as follows: flame retardants based on melamine and/or ammonium polyphosphate, bis(hexachlorocyclopentadieno)cyclooctane, tris-(2,3-dibromopropyl)isocyanurate, ethylenebistetrabromophthalimide, 1,2,5,6,9,10-hexabromocyclododecane, ethane-1,2-bis(pentabromophenyl), tris (3-bromo-2,2-(bromomethy)propyl)phosphate.

Further preferred flame retardants are chlorinated paraffin, 1,2-bis(tribromophenoxy)ethane, decabromobiphenyl, decabromodiphenylethane, decabromodiphenyl ether, octabromodiphenyl ether, ethylenebis(5,6-dibromonorbornane-2,3-dicarboximide), ethylenebis(tetrabromopthalimide), hexabromocyclododecane, tetrabromobisphenol A bis(2,3-dibromopropyl)ether. Particular preference is given to decabromodiphenylethane and hexabromocyclododecane.

The flame retardant is frequently comprised in an amount of 0.5 to 50% by weight, based on the inanimate organic materials, such as plastics (polymers) or coating materials, especially plastics, for example. The ratio of the flame retardant to the sterically hindered amines of the general formula (I), especially sterically hindered amines of the formula (I-a) to (I-t), is preferably in the range from 20:1 to 250:1.

One particularly advantageous embodiment of the inventive use comprises, as already mentioned above, in addition to the use of sterically hindered amines comprising one or more groups of the general formula (I), especially sterically hindered amines of the formula (I-a) to (I-t), the use of halogenated flame retardants. The use of this combination is that the sterically hindered amines comprising one or more groups of the general formula (I), especially sterically hindered amines of the formula (I-a) to (I-t), do not lose their activity in the presence of the halogenated flame retardants, whereas sterically hindered amines which are based on the corresponding N—H or N-alkyl derivatives are deactivated by the halogenated flame retardants.

The invention further provides a method of stabilizing inanimate organic materials, especially a method of protecting inanimate organic materials from the negative effects of electromagnetic radiation, especially light, heat or free radicals, in particular oxygen, which involves admixing the materials with sterically hindered amines comprising one or more groups of the general formula (I), more particularly sterically hindered amines of the general formulae (I-a) to (I-q), in an amount effective for stabilization, preferably in an amount of 0.01% to 5% by weight, preferably of 0.02% to 1% by weight, based on the inanimate organic material.

The invention further provides selected sterically hindered amines of the general formula (I-b) with $R^4$, $R^5$, $R^6$, and $R^7$ all being methyl, $R^8$ being hydrogen, $R^{10}$ being formyl, p being 2, $R^{11}$ being hexamethylene, $R^1$ being hydrogen, $R^2$ being hydrogen and $R^3$ being phenyl, it being possible for the phenyl radical $R^3$ to be substituted in each case at any position, up to five times, preferably not more than four times and more preferably not more than three times, by hydroxyl, amino, mono- or di-$C_1$-$C_{20}$ alkylamino, nitro, cyano, $CO_2M^1$, $CONM^1M^2$, $SO_3M^1$, $C_1$-$C_{20}$ alkyl, $C_1$-$C_{20}$ alkoxy, aryl, a heterocycle, heteroatoms or halogen and $M^1$ and $M^2$ each independently, alike or different, being H or $C_1$-$C_{20}$ alkyl. With particular preference, however, the phenyl $R^3$ is unsubstituted.

The invention further provides selected sterically hindered amines of the general formula (I-q) where $R^{20}$ is a mixture of $C_{18}$-$C_{22}$ alkyl groups, in particular a mixture of $C_{18}$-alkyl, $C_{20}$-alkyl, and $C_{22}$-alkyl. Particular preference is given here to steric amines of the formula (I-q) for which $R^{20}$ is a mixture of $C_{18}$-$C_{22}$-alkyl groups, in particular a mixture of $C_{18}$-alkyl, $C_{20}$-alkyl, and $C_{22}$-alkyl, and the majority (more than 50%) of the substituents $R^{23}$ correspond to a group —$OCR^1R^2R^3$. Here, $R^1$ and $R^2$ each independently, alike or different, are H, $C_1$-$C_{20}$ alkyl, $C_3$-$C_{15}$ cycloalkyl, aryl, hetaryl or a heterocycle, $R^3$ is aryl, or hetaryl, $R^4$, $R^5$, $R^6$, $R^7$ each independently, alike or different, are $C_1$-$C_{20}$-alkyl, or $R^4$ and $R^6$ or $R^5$ and $R^7$ together are a tetramethylene or pentamethylene group $R^{21}$ and $R^{22}$ each independently, alike or different, are H, $C_1$-$C_{20}$ alkyl, aryl, $C_1$-$C_{20}$ alkoxy, or $C_2$-$C_{20}$ alkenyl.

With preference here $R^1$ and $R^2$ each independently, alike or different are, H or $C_1$-$C_{20}$-alkyl, $R^3$ is aryl, $R^4$, $R^5$, $R^6$, $R^7$ each independently, alike or different, are $C_1$-$C_{20}$-alkyl.

With particular preference here $R^1$ and $R^2$ are H, $R^3$ is aryl, $R^4$, $R^5$, $R^6$, and $R^7$ are methyl.

The invention further provides selected sterically hindered amines of the general formula (I-r) where $R^4$, $R^5$, $R^6$, and $R^7$ each independently, alike or different, are $C_1$-$C_{20}$ alkyl, or $R^4$ and $R^6$ or $R^5$ and $R^7$ together are a tetramethylene or pentamethylene group, preferably $C_1$-$C_4$-alkyl, with particular preference all methyl, $R^{23}$ is —$OC(R^1R^2R^3)$ $R^1$ and $R^2$ each independently, alike or different, are H, $C_1$-$C_{20}$ alkyl, $C_3$-$C_{15}$ cycloalkyl, aryl, hetaryl or a heterocycle preferably both H, $R^3$ is aryl or hetaryl, preferably aryl, $R^{20}$ is $C_1$-$C_{30}$ alkyl, aryl, or a mixture of different $C_1$-$C_{30}$ alkyl, $R^{21}$ independently at each occurrence, alike or different, is H, $C_1$-$C_{20}$ alkyl, aryl, $C_1$-$C_{20}$ alkoxy or $C_2$-$C_{20}$ alkenyl, preferably $C_{16}$-$C_{22}$-alkyl, $R^{24}$ and $R^{25}$ each independently, alike or different, $C_1$-$C_{24}$ alkyl, preferably $C_{10}$-$C_{24}$-alkyl, more preferably $C_{14}$-$C_{22}$-alkyl, very preferably $C_{18}$-$C_{22}$-alkyl, $X^2$ is O or NH.

The invention further provides selected sterically hindered amines of the general formula (I-s) where $R^4$, $R^5$, $R^6$, and $R^7$ each independently, alike or different, are $C_1$-$C_{20}$ alkyl, or $R^4$ and $R^6$ or $R^5$ and $R^7$ together are a tetramethylene or pentamethylene group, preferably $C_1$-$C_4$-alkyl, with particular preference all methyl, $R^{23}$ is —$OC(R^1R^2R^3)$ $R^1$ and $R^2$ each independently, alike or different, are, H, $C_1$-$C_{20}$-alkyl, $C_3$-$C_{15}$-cycloalkyl, aryl, hetaryl or a heterocycle, preferably both H, $R^3$ aryl or hetaryl, preferably aryl, $R^{24}$ independently at each occurrence, alike or different, is $C_1$-$C_{24}$ alkyl, preferably $C_{10}$-$C_{24}$-alkyl, more preferably $C_{14}$-$C_{22}$-alkyl, very preferably $C_{18}$-$C_{22}$-alkyl.

The invention further provides selected sterically hindered amines of the general formula (I-t) where $R^4$, $R^5$, $R^6$, and $R^7$ each independently, alike or different, are, $C_1$-$C_{20}$ alkyl, or $R^4$ and $R^6$ or $R^5$ and $R^7$ together are a tetramethylene or pentamethylene group, preferably $C_1$-$C_4$-alkyl, with particular preference all methyl, $R^{23}$ is —$OC(R^1R^2R^3)$ $R^1$ and $R^2$ each independently, alike or different, are H, $C_1$-$C_{20}$ alkyl, $C_3$-$C_{15}$ cycloalkyl, aryl, hetaryl or a heterocycle, preferably both H, $R^3$ is aryl or hetaryl, preferably aryl, $R^{24}$ and $R^{25}$ each independently, alike or different, are $C_1$-$C_{24}$-alkyl, preferably $C_{10}$-$C_{24}$-alkyl, more preferably $C_{13}$-$C_{22}$-alkyl, very preferably $C_{18}$-$C_{22}$-alkyl, $X^2$ is O or NH.

Particular preference is also given here to sterically hindered amines of the general formula (I-t) with $R^{24}$ and $R^{25}$ alike or different and $C_{14}$-$C_{16}$-alkyl.

These selected sterically hindered amines are prepared by the processes described above for preparing the sterically hindered amines comprising one or more groups of the general formula (I) or sterically hindered amines of the formula (I-a) to (I-t).

The invention further provides materials, especially inanimate organic materials, comprising the above-described selected sterically hindered amines. These selected sterically hindered amines are comprised preferably in an amount of 0.01% to 5% by weight, more preferably of 0.02% to 1% by weight, based on the inanimate organic material. Likewise preferably the stabilized inanimate organic materials are plastics or coating materials, especially plastics as described above. Very preferably these plastics are agricultural films, PVC or flame-retardant thermoplastics.

EXAMPLES

Room temperature: 21° C.

Example 1

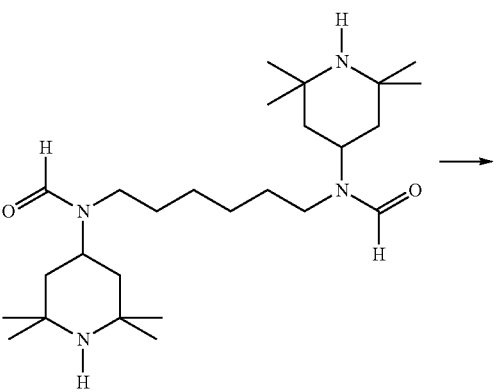

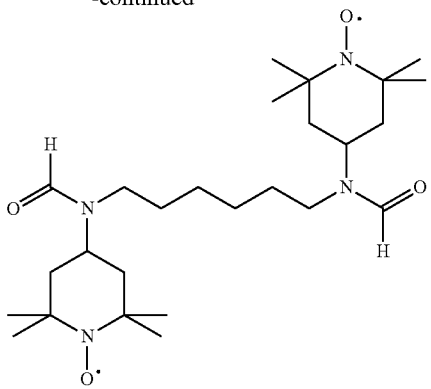

A solution of N,N'-bisformyl-N,N'-bis(2,2,6,6-tetramethyl-4-piperidinyl)hexamethylenediamine (Uvinul 4050 H from BASF SE) (49.00 g) in MeOH (480 ml) and H$_2$O (160 ml) was admixed with Na$_2$WO$_4$ (9.15 g) and H$_2$O$_2$ (30%, 65 ml) and stirred at room temperature for 24 hours. Suction filtration gave 50 g (96%) of the diradical as an orange solid. The product was used further without further purification.

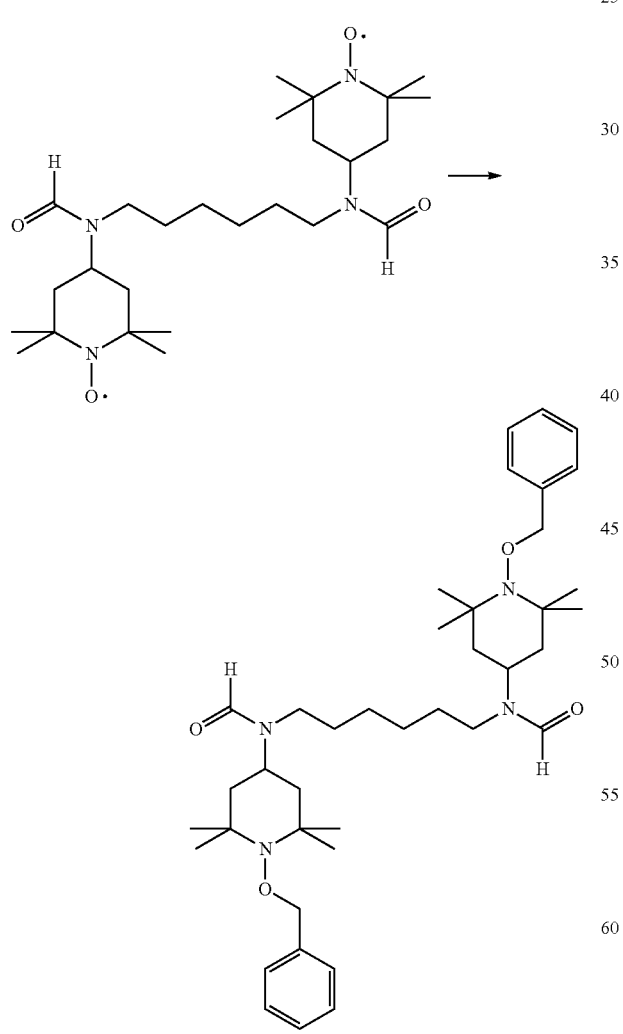

A mixture of benzyl bromide (7.12 g), nitroxyl radical from example 1 (12 g), copper powder (2.78 g), Cu(OTf)$_2$ (151 mg) and 4,4'-di-tert-butyl-2,2'-bipyridyl (referred to below as dTbPy) (0.45 g) in benzene (70 ml) was degassed and heated at reflux for 18 hours. After cooling to room temperature, the mixture was filtered to remove the residue. The filtrate was concentrated and purified by means of flash chromatography over silica gel (eluent 1:20 ethyl acetate/petroleum ether). The product was obtained as a white solid. $^1$H NMR (300 MHz, CDCl$_3$) δ 1.24-1.34 (m, 30 H), 1.62 (s, 6 H), 1.81 (dd, J=9.6, 22.8 Hz, 2 H), 3.23-3.40 (m, 4 H), 3.60-3.67 (m, 1.4 H), 4.51-4.56 (m, 0.7 H), 4.82 (s, 4 H), 7.27-7.36 (m, 10 H), 8.10-8.18 (m, 2 H).

Example 2

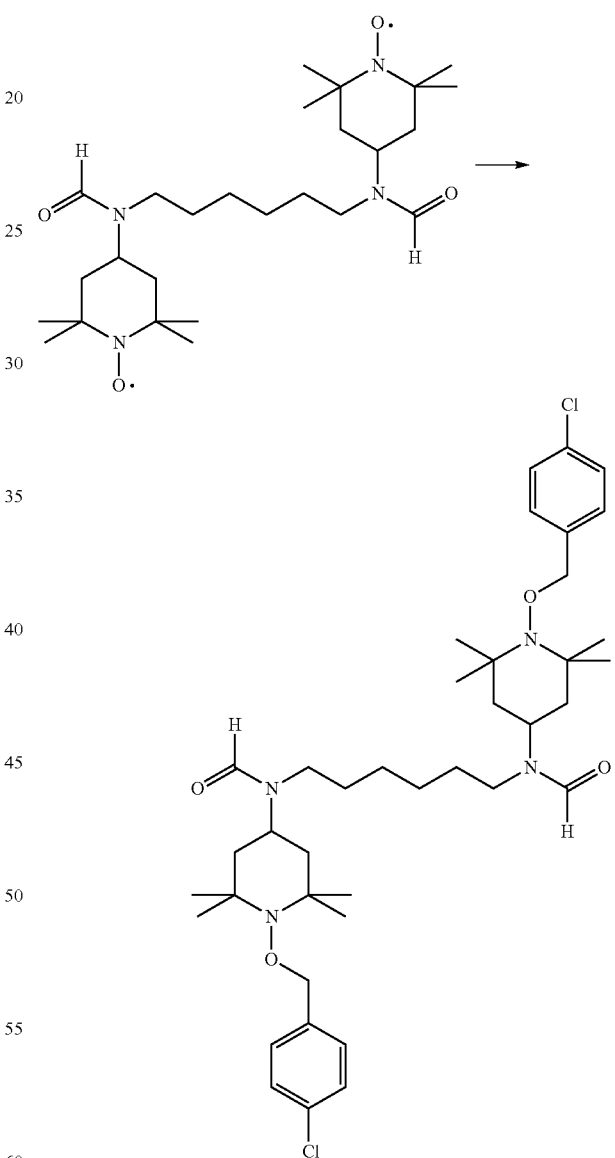

A degassed mixture of nitroxyl radicals from example 1 (50 g), copper powder (16.5 g), Cu(OTf)2 (750 mg mg) and dTbPy (1.95 g) in toluene (150 ml) was admixed with metering over the course of 5.5 hours at 75° C. with 4-chlorobenzyl bromide (53.3 g) and stirred at 75° C. for 2 hours more. After cooling to room temperature, it was filtered over alumina to remove the residue, and washed with toluene, and the filtrate was washed with 250 ml of 25% strength aqueous ammonia, the filtrate being concentrated and purified by means of flash chromagography over silica gel (eluent toluene/acetone). The product was obtained as a white solid. $^1$H NMR (300 MHz, CDCl$_3$) δ 1.24-1.34 (m, 30 H), 1.62 (s, 6 H), 1.81 (dd, J=9.6, 22.8 Hz, 2 H), 3.23-3.40 (m, 4 H), 3.60-3.67 (m, 1.4 H), 4.51-4.56 (m, 0.7 H), 4.82 (s, 4 H), 7.27-7.36 (m, 8 H), 8.10-8.18 (m, 2 H).

Example 3

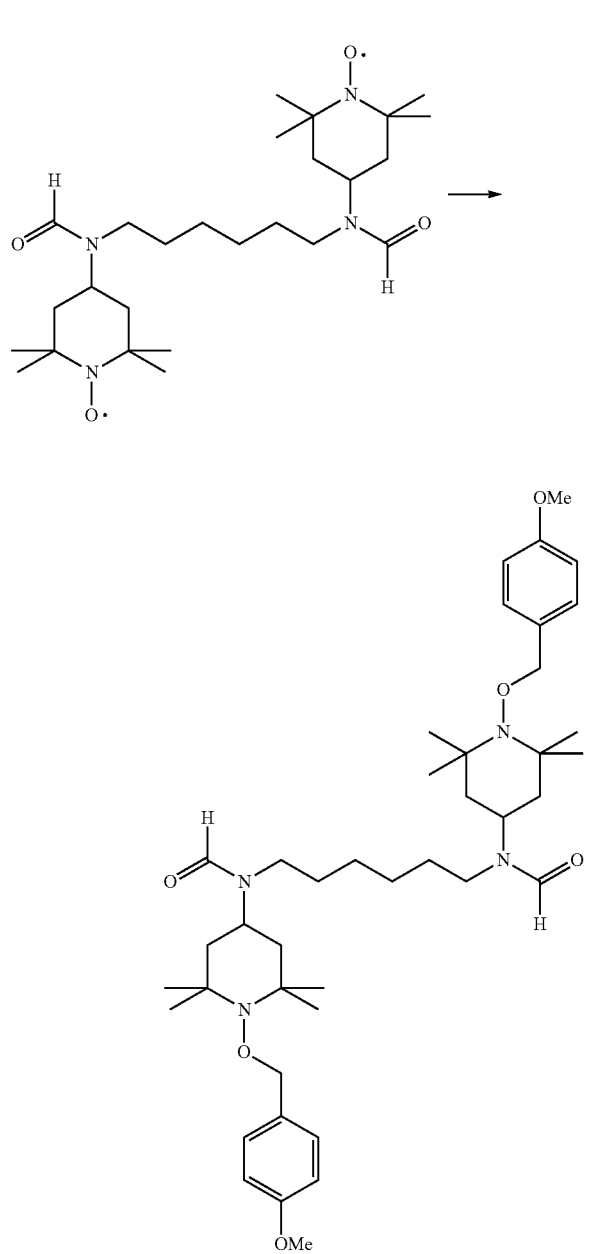

A degassed mixture of nitroxyl radical from example 1 (10 g), copper powder (3.3 g), Cu(OTf)2 (150 mg mg) and dTbPy (0.39 g) in toluene (30 ml) was admixed in metered form over the course of 6 hours at 75° C. with 4-methoxybenzyl bro-mide (10.4 g) and stirred at 75° C. for a further 20 hours. After cooling to room temperature, it was filtered over alumina to remove the residue, rinsed with toluene, and the filtrate was washed with 250 ml of 25% strength aqueous ammonia and concentrated, and purified by stirred extraction with methanol. The product was obtained as a white solid.

Example 4

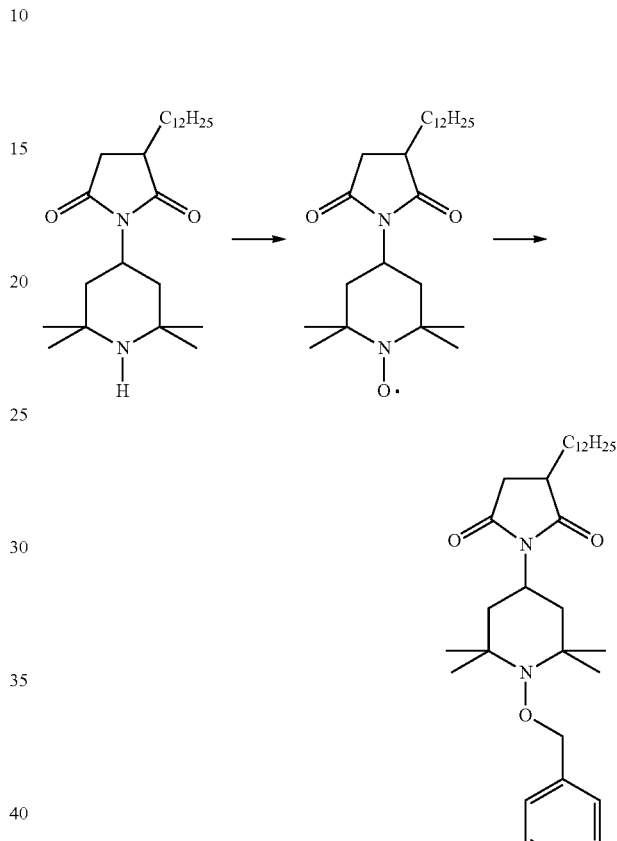

A solution of 3-dodecyl-1-(2,2,6,6-tetramethylpiperidin-4-yl)-pyrrolidin-2,5-dione (48.00 g) in MeOH (480 ml) was admixed with Na2WO4 (9.76 g) and H2O2 (30%, 145 ml) and stirred at room temperature for 5 hours. The reaction was quenched by addition of 300 ml of saturated thiosulfate solution, followed by extraction with tert-butyl ethyl ether (3×300 ml). The combined organic phases were dried and concentrated. This gave 46 g (92.5%) as a yellow oil. The product was used further, without further purification, as follows:

A mixture of benzyl bromide (4.87 g), nitroxyl radical (12 g), copper powder (1.9 g), Cu(OTf)$_2$ (100 mg) and dTbPy (0.31 g) in toluene (90 ml) was degassed and heated at reflux for 20 hours. After cooling to room temperature, it was filtered to remove the residue. The filtrate was concentrated and purified by means of flash chromatography over silica gel (eluent 1:20 ethyl acetate/petroleum ether). This gave 10.6 g (73%) of the product as a white solid. $^1$H NMR (300 MHz, CDCl$_3$) δ 0.88 (t, J=4.8 Hz, 3 H), 1.25-1.49 (m, 35 H), 1.84-1.92 (m, 1 H), 2.32 (dd, J=2.7, 12.9 Hz, 2 H), 2.51-2.56 (m, 2 H), 2.69-2.79 (m, 2 H), 4.40-4.48 (m, 1 H), 4.84 (s, 2 H), 7.28-7.35 (m, 5 H).

Example 5

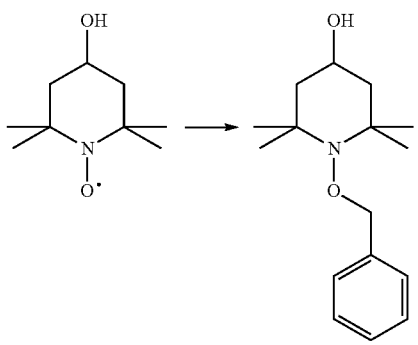

A mixture of benzyl bromide (12.5 g), 4-hydroxy-TEMPO (15 g), copper powder (4.9 g), Cu(OTf)$_2$ (260 mg) and dTbPy (0.8 g) in benzene (90 ml) was degassed and heated at reflux under a nitrogen atmosphere for 15 hours. After cooling to room temperature it was filtered to remove the residue. The filtrate was concentrated and purified by recrystallization from 1:20 ethyl acetate/petroleum ether). This gave 13.5 g (71%) of the product as a white solid. $^1$H NMR (300 MHz, CDCl$_3$) δ 1.19 (s, 6 H), 1.29 (s, 6 H), 1.49 (d, J=12.3 Hz, 2 H), 1.84 (dd, J=2.4, 12.3 Hz, 2 H), 3.92-4.04 (m, 1 H), 4.82 (s, 2 H), 7.25-7.37 (m, 5 H).

Example 6

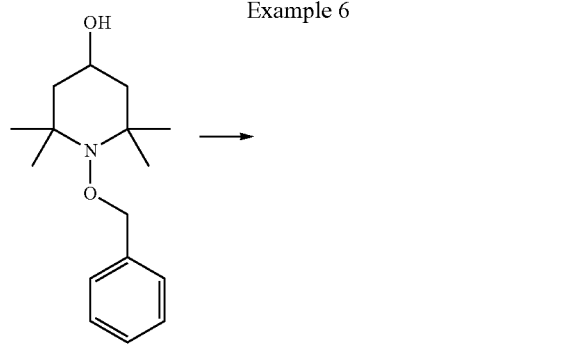

4.5 g of decanedioic dichloride were added dropwise over the course of 10 minutes to a stirred and cooled (0° C.) solution of 7.8 g of the benzyl compound from example 5, pyridine (7.1 g) and dimethylaminopyridine (DMAP, 0.8 g) in CH$_2$Cl$_2$ (100 ml). After the addition the cooling bath was removed and the mixture was stirred further at room temperature for 5 hours. Then a saturated solution of ammonium chloride was added and the system was extracted with three times 100 ml of ethyl acetate. The organic phases were dried over sodium sulfate and concentrated. Flash chromatography over silica gel (eluent 1:30 ethyl acetate/petroleum ether) afforded 6.2 g of the desired product as a white solid. $^1$H NMR (300 MHz, CDCl$_3$) δ 1.25-1.30 (m, 34 H), 1.60 (t, J=9.0 Hz, 6 H), 1.85 (d, J=9.9 Hz, 4 H), 2.26 (t, J=7.5 Hz, 4 H), 4.82 (s, 4 H), 5.01-5.08 (m, 2 H), 7.28-7.35 (m, 10 H).

Example 7

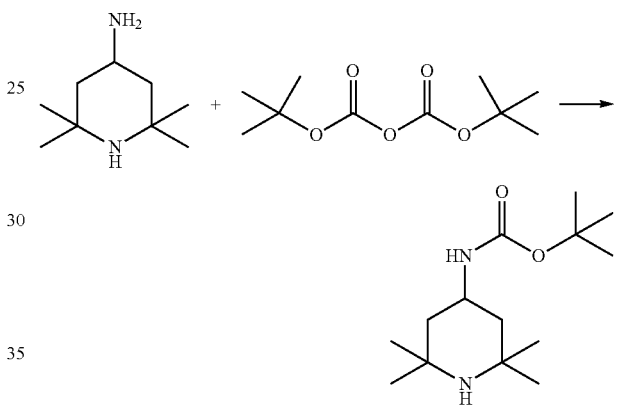

Added dropwise at room temperature and with cooling to an initial charge of 156.3 g (1.0 mol) of triacetonediamine in 2000 ml of dichloromethane under a nitrogen atmosphere were 90.0 g (0.4 mol) of di-tert-butyl dicarbonate, in 97% form. The reaction solution was then stirred at room temperature for 3 days more. It was admixed with 1000 ml of water. The organic phase was extracted with twice 500 ml of water, and the aqueous phase with 500 ml of dichloromethane. The combined organic phases were dried over Na$_2$SO$_4$, and were concentrated completely on a rotary evaporator following filtration. This gave 91.1 g of pale yellow crystals (89%). Mp.: 180°-181° C.

Example 8

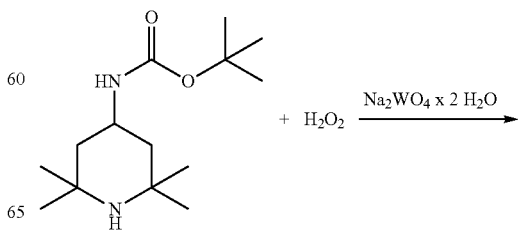

-continued

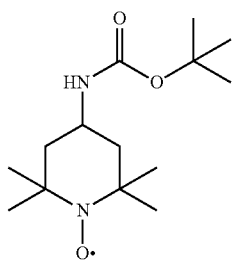

10.1 g (39.4 mmol) of the compound from example 7 were introduced as an initial charge in 250 ml of methanol and 88 ml of distilled water, 2.2 g (6.6 mmol) of $Na_2WO_4 2H_2O$ were added, and 89.3 g (788 mmol) of $H_2O_2$ in 30% form were added dropwise at room temperature over the course of 10 minutes. The mixture was stirred at 60° C. for 12 hours, cooled to room temperature, and filtered with suction, and the solid product was rinsed with water. This gave 9.5 g of orange crystals (89% yield) with a melting point of 199°-200° C.

Example 9

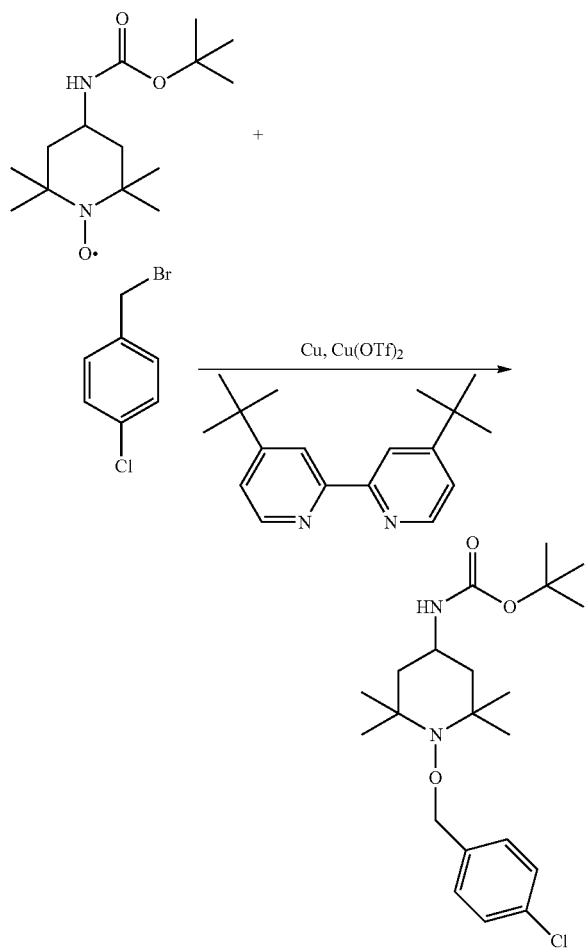

9.0 g (33 mmol) of the compound from example 8, 2.0 g (32 mmol) of copper powder, 0.54 g (1.5 mmol) of $Cu(OTf)_2$ (copper triflate), 1.64 g (6.0 mmol) of 4,4'-di-tert-butyl-2,2'-bipyridyl, in 98% form, and 6.2 g (30 mmol) of 4-chlorobenzyl bromide were stirred at 90° C. under a nitrogen atmosphere in 100 ml of toluene for 12 hours. The reaction solution was filtered over silica gel at room temperature and the solid product was rinsed with toluene and extracted with twice 100 ml of 1-2% ammonia solution and with once 100 ml of water. The organic phase was dried over $Na_2SO_4$ and concentrated fully under reduced pressure, following filtration. This gave 5.7 g of yellow crystals (48%).

Example 10

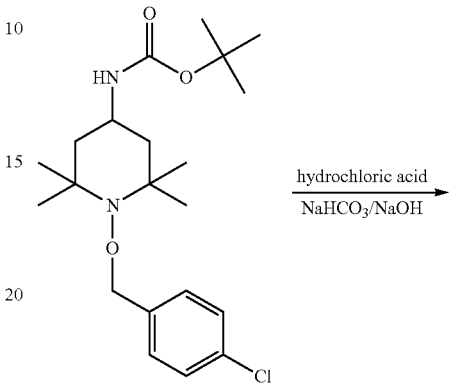

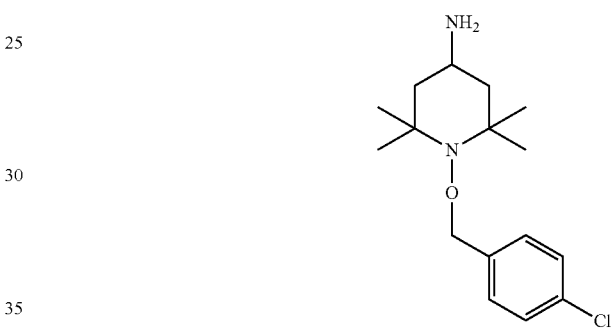

Under a nitrogen atmosphere, 5.4 g (13.6 mmol) of the compound from example 9 were stirred with 30 ml of hydrochloric acid (10% strength) and 50 ml of ethyl acetate at 90° C. for 2 hours.

After cooling had taken place, 100 ml of saturated $NaHCO_3$ solution and 80 ml of 10% strength NaOH were added slowly (pH 10). This was followed by extraction with twice 100 ml of ethyl acetate, and the organic phase was extracted with 100 ml of water. After drying over $Na_2SO_4$, the organic phase was concentrated completely at 40° C./10 mbar. This gave 3.4 g of beige crystals (85%).

Example 11

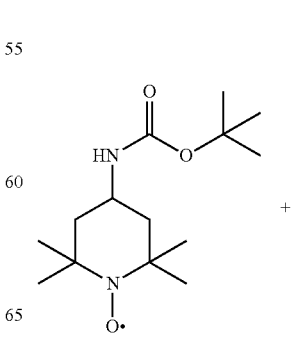

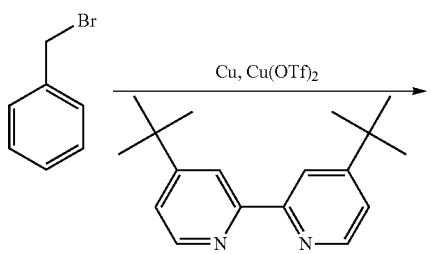

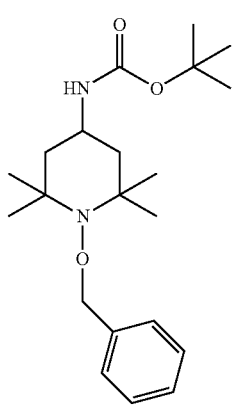

88.1 g (0.325 mol) of the compound from example 8, 19.5 g (0.315 mol) of copper powder, 5.48 g (0.015 mol) of Cu(OTf)$_2$ (copper triflate),16.15 g (0.059 mol) of 4,4'-di-tert-butyl-2,2'-bipyridyl, in 98% form, and 56.14 g (0.295 mol) of benzyl bromide, in 98% form, were stirred in 1000 ml of toluene at an internal temperature of 90° C. for 16 hours.

The reaction solution was filtered over silica gel at room temperature and the solid product was rinsed with toluene and concentrated completely on a rotary evaporator. This gave 82.0 g of yellow crystals (70%).

Example 12

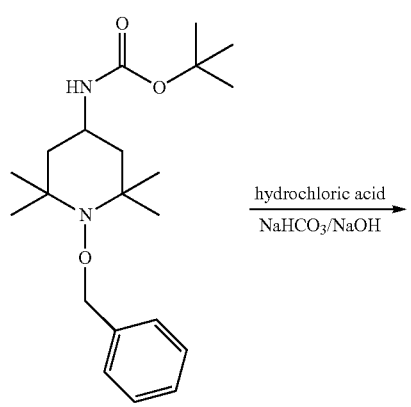

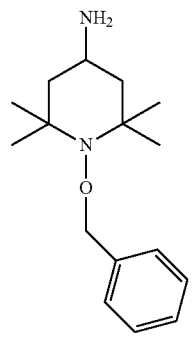

82.0 g (0.226 mol) of the compound from example 11 were dissolved in 770 ml of ethyl acetate, 462 ml of 10% strength hydrochloric acid were added dropwise at room temperature, and the mixture was stirred at 90° C. for 2 hours. After cooling to room temperature, the reaction solution was rendered alkaline in a glass beaker with 2000 ml of saturated NaHCO$_3$ solution and 237 g of 50% NaOH, to a pH of 9. The phases were separated. The aqueous phase was extracted with twice 250 ml of glacial acetic acid, and the organic phase was extracted with 250 ml of water. Drying over sodium sulfate and subsequent filtration were followed by complete concentration under reduced pressure. This gave 54.9 g of pale brown, semicrystalline oil (93%).

Example 13

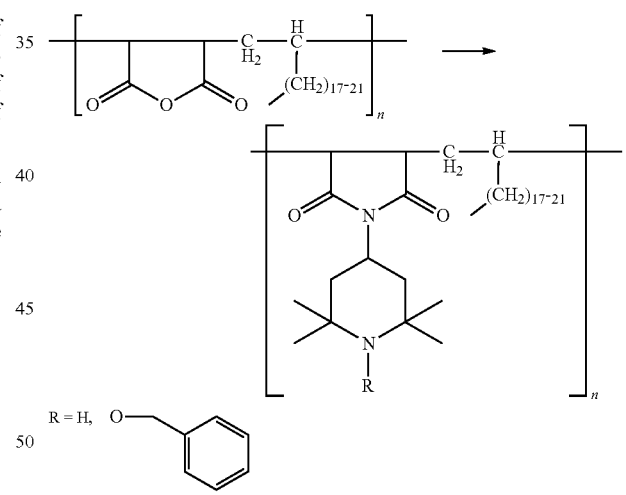

A mixture of 10.3 g of the compound from example 12, benzylated TAD (triacetonediamine) and 24.5 g of triacetonediamine was introduced as an initial charge in 50 g of Solvesso 100 (hydrocarbon solvent with high fraction of aromatic compounds), and this initial charge was heated to 190° C., and, under a nitrogen atmosphere, 94.5 g of a copolymer of maleic anhydride and olefin (average molar mass approximately 3500) in a dropping funnel heated at 150° C. were added dropwise over the course of 80 minutes. Stirring was continued at 190° C. for 4 hours, and, after cooling had taken place, the Solvesso was concentrated on a rotary evaporator with an oil pump vacuum of 3 mbar and a bath temperature of 120° C. This gave 120 g of a glasslike residue.

Onset temperature: 400° C.

Comparative Example 1

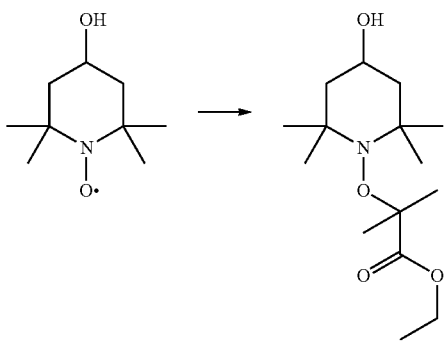

A mixture of ethyl 2-bromo-2-methylpropionate (12.5 g), 4-hydroxy-TEMPO (20 g), copper powder (7.76 g), Cu(OTf)$_2$ (420 mg) and dTbPy (1.25 g) in benzene (120 ml) was degassed and heated at reflux under a nitrogen atmosphere for 30 hours. After cooling to room temperature it was filtered to remove the residue. The filtrate was concentrated and purified by means of column chromatography using 1:30 ethyl acetate/petroleum ether. This gave 4.6 g (15%) of the product as a white solid. $^1$H NMR (300 MHz, CDCl$_3$) δ 1.16 (s, 6 H), 1.21 (s, 6 H), 1.29 (t, J=5.7 Hz, 3 H), 1.41-1.50 (m, 8 H), 1.81 (dd, J=1.2, 3.3 Hz, 2 H), 3.91-3.98 (m, 1 H), 4.17 (dd, J=5.4, 10.8 Hz, 2 H).

Comparative Example 2

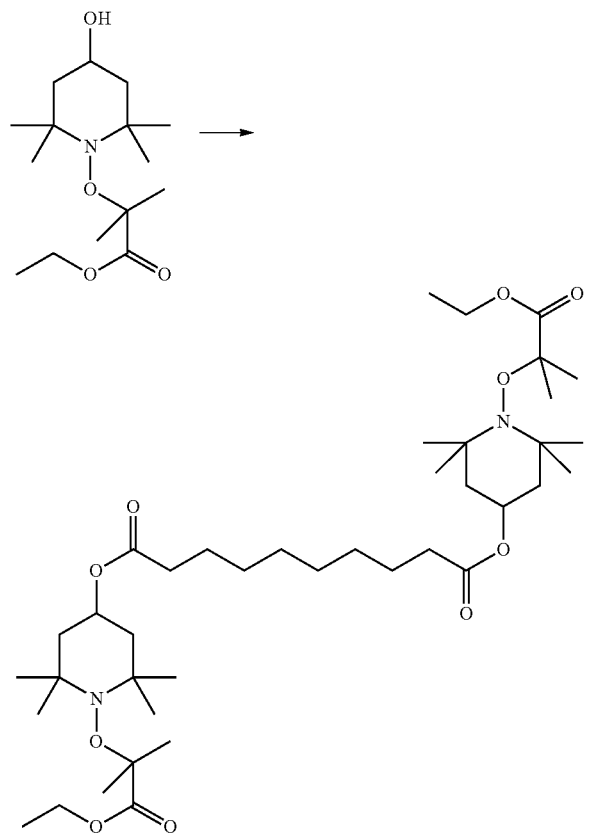

0.88 g of decanedioic dichloride was added dropwise over the course of 10 minutes to a stirred and cooled (0° C.) solution of 2.1 g of the resulting compound from example 7, pyridine (2.3 g) and dimethylaminopyridine (DMAP, 0.2 g) in CH$_2$Cl$_2$ (30 ml). Following the addition, the cooling bath was removed and the mixture was stirred further for 16 hours at room temperature. Then a saturated solution of ammonium chloride was added and the product was extracted with three times 50 ml of ethyl acetate. The organic phases were dried over sodium sulfate and concentrated. Flash chromatography over silica gel (eluent 1:20 ethyl acetate/petroleum ether gave 1.75 g of the desired product as a white solid. $^1$H NMR (300 MHz, CDCl$_3$) δ 1.03 (s, 12 H), 1.24-1.31 (m, 26 H), 1.46-1.51 (m, 20 H), 1.55-1.58 (m, 2 H), 1.84 (dd, J=4.2, 12.8 Hz, 4 H), 2.24 (t, J=7.5 Hz, 4 H), 4.16 (dd, J=7.2, 14.4 Hz, 2 H), 4.95-5.06 (m, 2 H).

Comparative Example 3

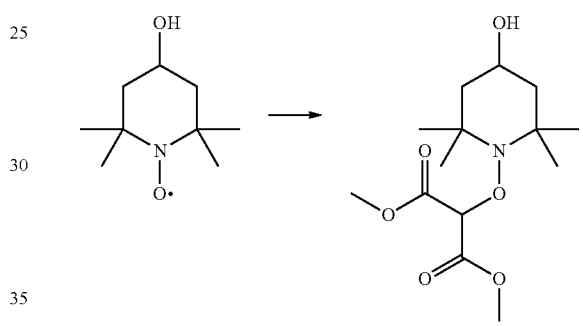

A mixture of dimethylbromomalonate (36.60 g), 4-hydroxy-TEMPO (30 g), copper powder (11.63 g), Cu(OTf)$_2$ (630 mg) and dTbPy (1.85 g) in benzene (200 ml) was degassed and heated at reflux for 20 hours under a nitrogen atmosphere. After cooling to room temperature it was filtered to remove the residue. The filtrate was concentrated and purified by means of column chromatography using 1:10 ethyl acetate/petroleum ether. This gave 9.1 g (19%) of the product as a white solid. $^1$H NMR (300 MHz, CDCl$_3$) δ 1.08 (s, 6 H), 1.24 (s, 6 H), 1.43 (t, J=9.3 Hz, 2 H), 1.65 (d, J=3.3 Hz, 1 H), 1.80 (dd, J=1.8, 8.1 Hz, 2 H), 3.77 (s, 6 H), 3.91-3.99 (m, 1 H).

Comparative Example 4

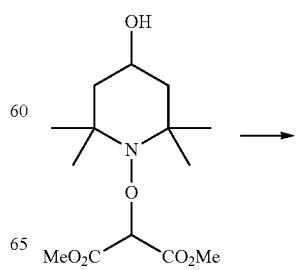

-continued

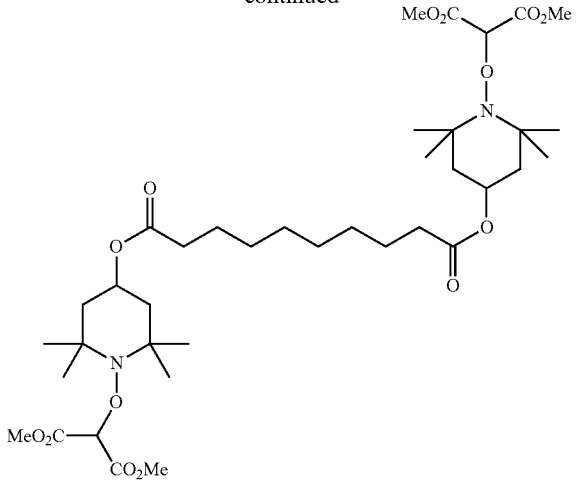

2.5 g of decanedioic dichloride were added dropwise over the course of 10 minutes to a stirred and cooled (0° C.) solution of 6 g of the resulting compound from example 9, pyridine (6.25 g) and dimethylaminopyridine (DMAP, 0.5 g) in $CH_2Cl_2$ (80 ml). Following the addition the cooling bath was removed and the mixture was stirred further at room temperature for 15 hours. Then a saturated solution of ammonium chloride was added and extraction was carried out with three times 100 ml of ethyl acetate. The organic phases were dried over sodium sulfate and concentrated. Flash chromatography over silica gel (eluent 1:20 ethyl acetate/petroleum ether gave 3.4 g (46%) of the desired product as a white solid. $^1$H NMR (300 MHz, $CDCl_3$) δ 1.09 (s, 12 H), 1.23-1.29 (m, 20H), 1.47-1.57 (m, 8 H), 1.83 (dd, J=3.0, 6.3 Hz, 4 H), 2.23 (t, J=5.7 Hz, 4 H), 3.78 (s, 12 H), 4.94 (s, 2 H), 4.97-5.03 (m, 2 H).

Comparative Example 5

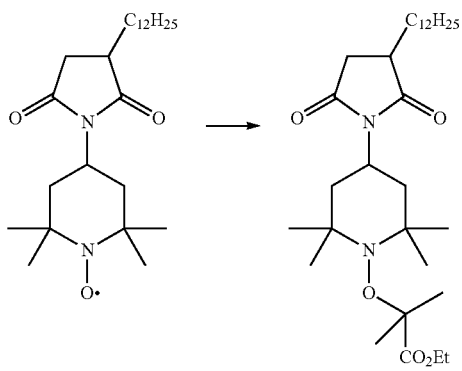

A mixture of ethyl 2-bromo-2-methylpropionate (6.91 g), nitroxyl radical from example 4 (15.00 g), copper powder (2.38 g), $Cu(OTf)_2$ (130 mg) and dTbPy (0.38 g) in 2-ethoxyethanol (100 ml) was degassed and heated at 70° C. for 5 hours under a nitrogen atmosphere. After cooling to room temperature it was filtered to remove the residue. The filtrate was concentrated and purified by means of column chromatography using 1:100 ethyl acetate/petroleum ether. This gave 1.81 g (11%) of the product as a white solid. $^1$H NMR (300 MHz, $CDCl_3$) δ 0.85 (d, J=3.2 Hz, 2 H), 0.86 (d, J=10.6 Hz, 2 H), 1.12 (s, 6 H), 1.24-1.46 (m, 31 H), 1.46 (s, 6 H), 1.82-1.87 (m, 1 H), 2.29 (dd, J=3.0, 13.2 Hz, 1 H), 2.44 (t, J=9.3 Hz, 2 H), 2.63-2.77 (m, 2 H), 4.15 (dd, J=5.4, 10.8 Hz, 2H), 4.35-4.42 (m, 1H).

Example 14

Squalane Test for Simulating Polymer Stabilization Under Thermooxidative Conditions In a storage experiment, squalane, which was used as a liquid polyolefin substitute, was subjected to oxidative degradation at 75° C. in the presence of the free-radical initiator "BUT" [2,2,-di(tert-butylperoxy)butane]. The degradation was monitored by GC chromatography or Raman spectroscopy. The Raman spectral range evaluated was 3290 $cm^{-1}$ to 2560 $cm^{-1}$ (CH range) and 1530 $cm^{-1}$ to 700 $cm^{-1}$.

Through the addition of stabilizers it was possible to prevent or retard the degradation of squalane. The degradation retarded through the use of a stabilizer allowed the activity of these compounds to be assessed.

In the experiment, 3 g of squalane (7.1 mmol), 0.06 g of a "BUT" solution (50% strength solution, 0.3 mmol BUT), and the compound under investigation (0.15% by weight) were introduced into a test tube. The resulting solution or suspension was heated to 75° C. with shaking, and the degradation was monitored by means of GC monitoring or Raman spectroscopy.

TABLE 1

Squalane content after a number of days [d], in % of the initital value

| | Squalane content | | | | | | | | | | |
|---|---|---|---|---|---|---|---|---|---|---|---|
| | 2 d | 5 d | 9 d | 12 d | 15 d | 22 d | 29 d | 36 d | 43 d | 50 d | 56 d |
| Ex. 1 | 95.3 | 95.6 | 97.5 | 95.5 | 96.1 | 95.1 | 95.5 | 95.1 | 96.7 | 95.7 | 96.6 |
| CS1 | 95.1 | 95.2 | 94.3 | 92.5 | 92.1 | 91.0 | 89.1 | 88.4 | 86.9 | 88.0 | 87.1 |
| REF | 98.1 | 91.6 | 87.1 | 76.4 | 72.3 | 69.2 | 58.7 | 48.6 | 47.1 | 39.4 | 34.9 |

Comparison substance (CS 1): decanedioic acid bis(2,2,6,6-tetramethyl-1,octyloxypiperidin-4-yl) ester (not inventive, Tinuvin® 123)

Reference without stabilizer (REF): squalane with BUT

Example 15

Squalane Test for Simulating Polymer Stabilization Under Thermooxidative Conditions in the Presence of Agrochemicals In a storage experiment, squalane, which was used as a liquid polyolefin substitute, was subjected to oxidative degradation at 75° C. in the presence of the free-radical initiator "BUT" [2,2,-di(tert-butylperoxy)butane]. The degradation was monitored by GC chromatography or Raman spectroscopy. The Raman spectral range evaluated was 3290 cm$^{-1}$ to 2560 cm$^{-1}$ (CH range) and 1530 cm$^{-1}$ to 700 cm$^{-1}$.

Through the addition of stabilizers it was possible to prevent or retard the degradation of squalane. The degradation retarded through the use of a stabilizer allowed the activity of these compounds to be assessed. In the presence of agrochemicals, the protective effect observed for the stabilizers was reduced, but this reduction was much smaller with the compounds of the invention.

0.0045 g (0.15%) in each case of the stabilizer, and 0.0045 g (0.15%) of the agrochemical, were weighed out into a lipless test tube, and made up with 3 g of a solution of 2% 2,2-bis(tert-butylperoxy)butane (50 wt % in mineral oil) in squalane.

The resulting solution or suspension was heated to 75° C. with shaking, and the degradation was ascertained by GC monitoring or Raman spectroscopy after 43 days.

|  | Ex. 1 | CS2 | CS3 | CS4 |
|---|---|---|---|---|
| Squalane content without agrochemical | 96.7 | 92.3 | 87.2 | 90.8 |
| Metiram ® (CAS 9006-42-2) | 87.4 | 63.6 | n.a. | 56.9 |
| Mancozeb ® (CAS 8018-01-7) | 96.3 | 86.9 | 80.4 | 82.5 |

Comparison substance (CS2): (noninventive, Chimassorb ® 119, CAS 106990-43-6)
Comparison substance (CS3): (noninventive, Chimassorb ® 944, CAS 71878-19-8)
Comparison substance (CS4): (noninventive, Tinuvin ® NOR 371, CAS2800-4000)

Example 16

Onset temperature: the temperature stability of the compounds was determined by thermogravimetric measurement in a platinum crucible under air. For this purpose, samples were each weighed in to a crucible, heated to 600° C. at a heating rate of 10° C./min, and measured for weight loss. The onset temperature describes the beginning of the decrease in weight.

| Radical = | Sample 1 | Sample 2 | Sample 3 | Sample 4 |
|---|---|---|---|---|
| 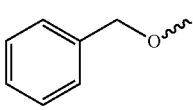 | 258 | 253 | 255 | 208 |
|  | 256 | not determined | not determined | not determined |
|  | 247 | not determined | not determined | not determined |
| 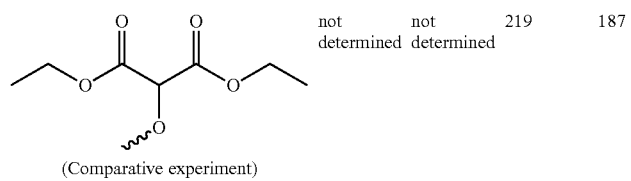 (Comparative experiment) | not determined | not determined | 219 | 187 |

-continued
| Radical = | Sample 1 | Sample 2 | Sample 3 | Sample 4 |
|---|---|---|---|---|
| 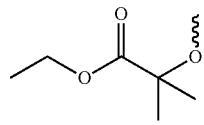<br>(Comparative experiment) | not determined | 152 | 151 | 142 |
Sample 1:
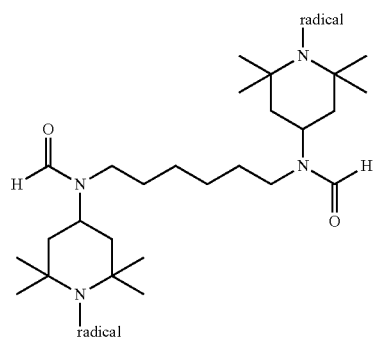
Sample 2:
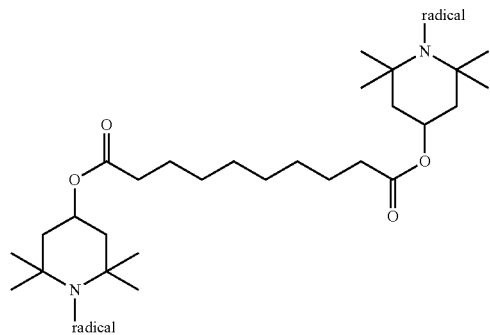
Sample 3:
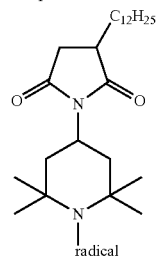
Sample 4:
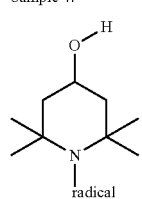

Example 17

Production of an Inventive LDPE Film 1000 g of Lupolen 1840 D (LDPE, Basel) and 3 g of the compound from example 1 were intimately mixed and extruded using a twin-screw extruder. The resulting compound was then processed on a blow-molding line to a 100 μm thick blown film.

Comparative Example 6

Production of a Non-Inventive LDPE Film

In the same way as in example 9, a film was produced, but instead of the compound from example 1 it comprised 3 g of N,N'-bisformyl-N,N'-bis(2,2,6,6-tetramethyl-4-piperidinyl) hexamethylenediamine (CAS No. 124172-53-8, Uvinul® 4050 H, BASF SE).

Example 18

Artificial Weathering of the LDPE Films

The films from example 9 and comparative example 6 were subjected to artificial weathering in accordance with standard DIN EN ISO 4892-2. A measurement was made of the time taken for the films to become brittle. The results are set out in the table below:

|  | Stabilizer | Time to embrittlement |
|---|---|---|
| 10a film from example 9 | Compound from example 1 | >14400 h |
| 10b film from comparative example 6 | N,N'-bisformyl-N,N'-bis(2,2,6,6-tetramethyl-4-piperidinyl)hexamethylenediamine | 2000 h |

The invention claimed is:

1. A sterically hindered amine of formula (2)

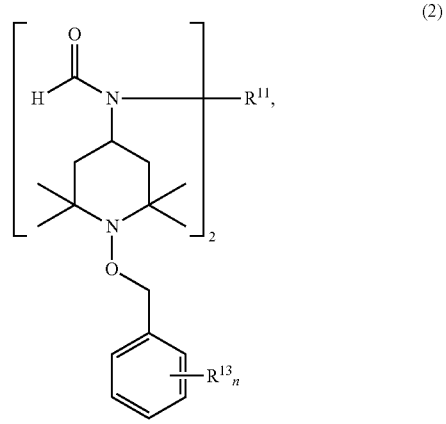

(2)

wherein $R^{11}$ is hexamethylene, $R^{13}$ is selected from the group consisting of hydrogen, hydroxyl, amino, mono-$C_1$-$C_{20}$ alkylamino, di-$C_1$-$C_{20}$ alkylamino, nitro, cyano, $CO_2M^1$, $CONM^1M^2$, $SO_3M^1$, $C_1$-$C_{20}$ alkyl, $C_1$-$C_{20}$ alkoxy, aryl, a heterocycle, a heteroatom, and a halogen, and $M^1$ and $M^2$ each independently, alike or different, is H or $C_1$-$C_{20}$ alkyl, and n is an integer from 1 to 5.

2. The sterically hindered amine of claim 1, wherein $R^{13}$ is, in each case, hydrogen.

* * * * *